(12) United States Patent
Amanatullah et al.

(10) Patent No.: US 10,194,990 B2
(45) Date of Patent: Feb. 5, 2019

(54) METHOD FOR AUGMENTING A SURGICAL FIELD WITH VIRTUAL GUIDANCE CONTENT

(71) Applicant: Arthrology Consulting, LLC, Palo Alto, CA (US)

(72) Inventors: Derek Amanatullah, Palo Alto, CA (US); Matthew L Hasel, Redwood City, CA (US); Ian Börk, Redwood City, CA (US); Sarah M Hegmann, Redwood City, CA (US)

(73) Assignee: Arthrology Consulting, LLC, Palo Alto, CA (US)

( * ) Notice: Subject to any disclaimer, the term of this patent is extended or adjusted under 35 U.S.C. 154(b) by 0 days.

(21) Appl. No.: 15/499,046

(22) Filed: Apr. 27, 2017

(65) Prior Publication Data

US 2017/0312031 A1    Nov. 2, 2017

Related U.S. Application Data

(60) Provisional application No. 62/328,330, filed on Apr. 27, 2016, provisional application No. 62/363,022, filed on Jul. 15, 2016.

(51) Int. Cl.
*A61B 17/32* (2006.01)
*A61B 17/56* (2006.01)
(Continued)

(52) U.S. Cl.
CPC .............. *A61B 34/10* (2016.02); *A61B 17/16* (2013.01); *A61B 34/20* (2016.02); *G06T 7/0012* (2013.01); *G06T 7/344* (2017.01); *G06T 19/006* (2013.01); *G09B 5/02* (2013.01); *G09B 23/28* (2013.01); *G09B 23/30* (2013.01); *A61B 2034/101* (2016.02); *A61B 2034/102* (2016.02); *A61B 2034/107* (2016.02);
(Continued)

(58) Field of Classification Search
None
See application file for complete search history.

(56) References Cited

U.S. PATENT DOCUMENTS 9,866,767 B2 *    1/2018   Jones ...................... H04N 5/272
2006/0015120 A1 * 1/2006   Richard ................. A61B 90/06
                                                                    606/102
(Continued)

*Primary Examiner* — Tize Ma
(74) *Attorney, Agent, or Firm* — Run8 Patent Group, LLC; Peter Miller; Alexander R. Flake

(57) ABSTRACT

One variation of a method for augmenting a surgical field with virtual guidance content includes: accessing a scan representing a tissue of a patient; combining the scan with a generic virtual anatomical model to define a custom virtual anatomical model of the tissue; defining a cut trajectory along an intersection between a virtual model of a surgical implant and the custom virtual anatomical model of the tissue; aligning a virtual cut surface to the cut trajectory to locate the virtual model of the surgical guide relative to the custom virtual anatomical model; accessing an image of a surgical field; detecting the tissue in the image; aligning the custom virtual anatomical model to the tissue detected in the image; defining a target real location for a real surgical guide in the surgical field; and generating a frame depicting the target real location of the surgical guide in the surgical field.

21 Claims, 13 Drawing Sheets

(51) Int. Cl.
    *G06T 19/00*     (2011.01)
    *G06T 19/20*     (2011.01)
    *A61B 34/10*     (2016.01)
    *G09B 23/30*     (2006.01)
    *G09B 5/02*     (2006.01)
    *A61B 34/20*     (2016.01)
    *A61B 17/16*     (2006.01)
    *G06T 7/33*     (2017.01)
    *G06T 7/00*     (2017.01)
    *G09B 23/28*     (2006.01)

(52) U.S. Cl.
    CPC ........... *G06T 2207/10016* (2013.01); *G06T 2207/10028* (2013.01); *G06T 2207/10116* (2013.01); *G06T 2207/30008* (2013.01); *G06T 2210/41* (2013.01)

(56) References Cited

U.S. PATENT DOCUMENTS

| | | | | |
|---|---|---|---|---|
| 2012/0308963 A1* | 12/2012 | Hasselgren | ......... | A61C 8/0036 433/201.1 |
| 2013/0060146 A1* | 3/2013 | Yang | ...................... | A61B 5/055 600/476 |
| 2013/0211792 A1* | 8/2013 | Kang | ................... | G16H 50/50 703/1 |
| 2016/0191887 A1* | 6/2016 | Casas | ................... | H04N 13/296 348/47 |
| 2016/0324580 A1* | 11/2016 | Esterberg | ............... | A61B 34/10 |

\* cited by examiner

METHOD FOR AUGMENTING A SURGICAL FIELD WITH VIRTUAL GUIDANCE CONTENT

CROSS-REFERENCE TO RELATED APPLICATIONS

This Application claims the benefit of U.S. Provisional Application No. 62/328,330, filed on 27 Apr. 2016, and U.S. Provisional Application No. 62/363,022, filed on 15 Jul. 2016, both of which are incorporated in their entireties by this reference.

TECHNICAL FIELD

This invention relates generally to the field of augmented reality and more specifically to a new and useful method for augmenting a surgical field with virtual guidance content in the field of augmented reality.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. First Method

Figure 1:
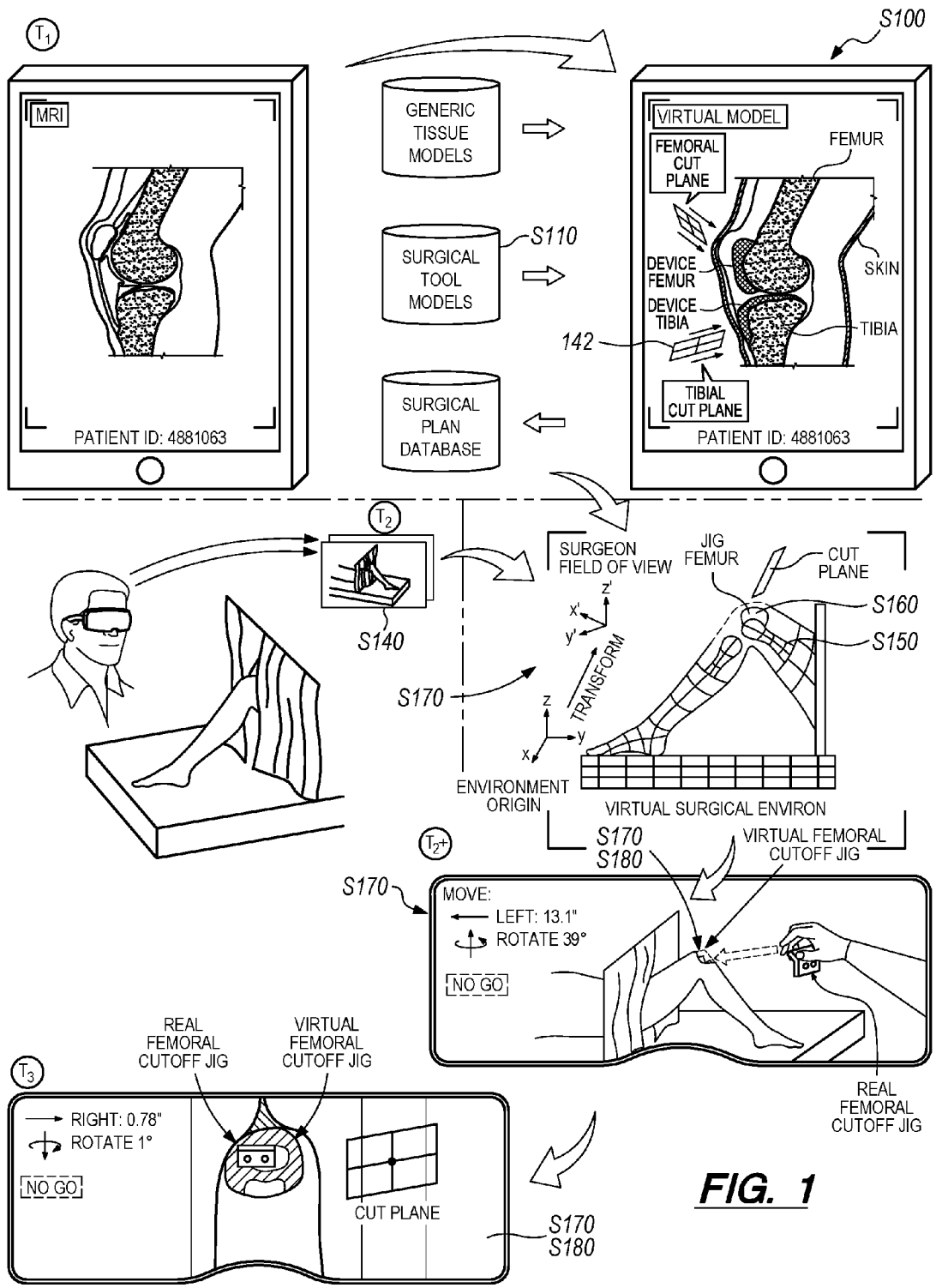
FIG. 1 is a flowchart representation of a first method.
Figure 3A:
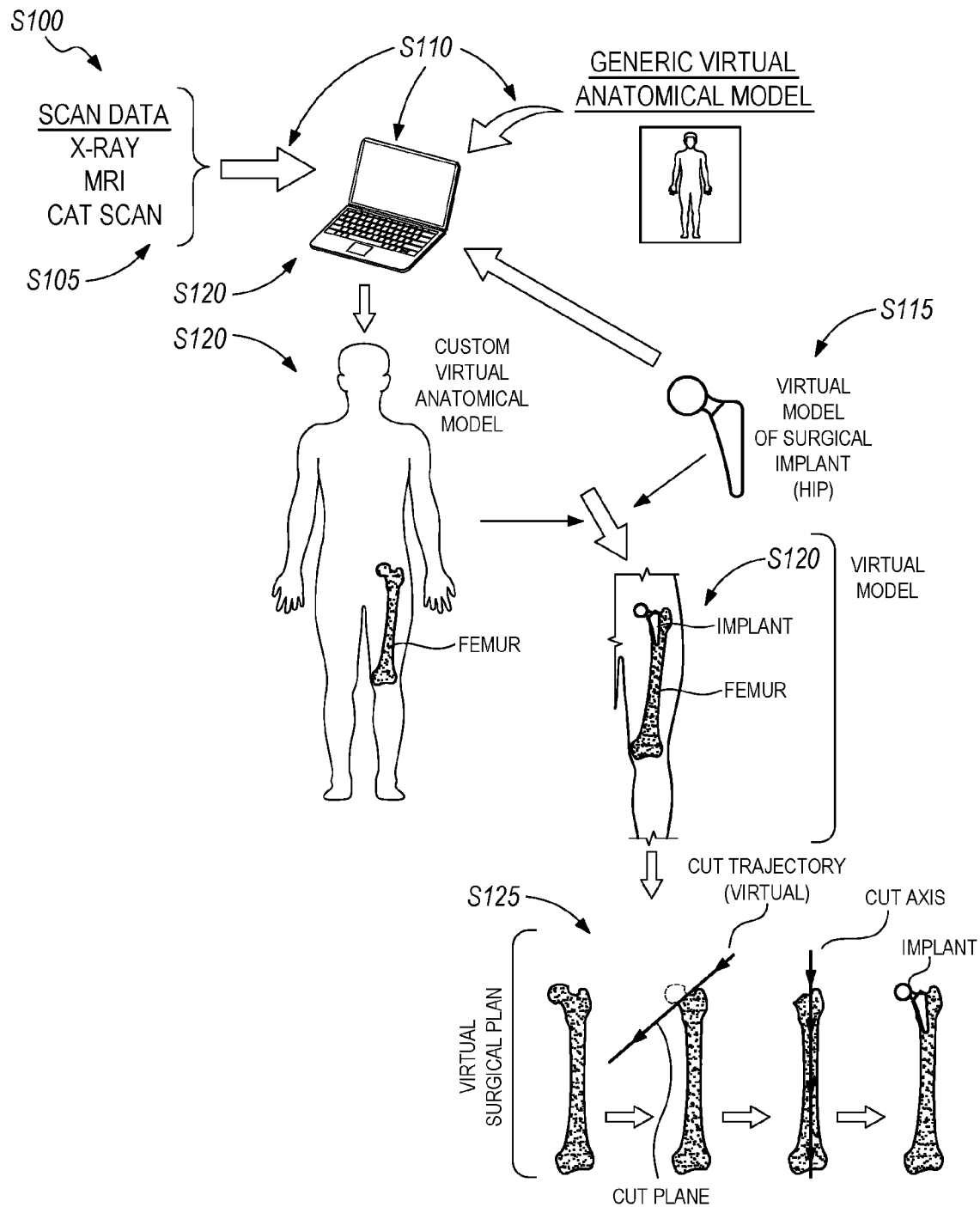
FIGS. 3A and 3B are flowchart representations of the first method.
Figure 3B:
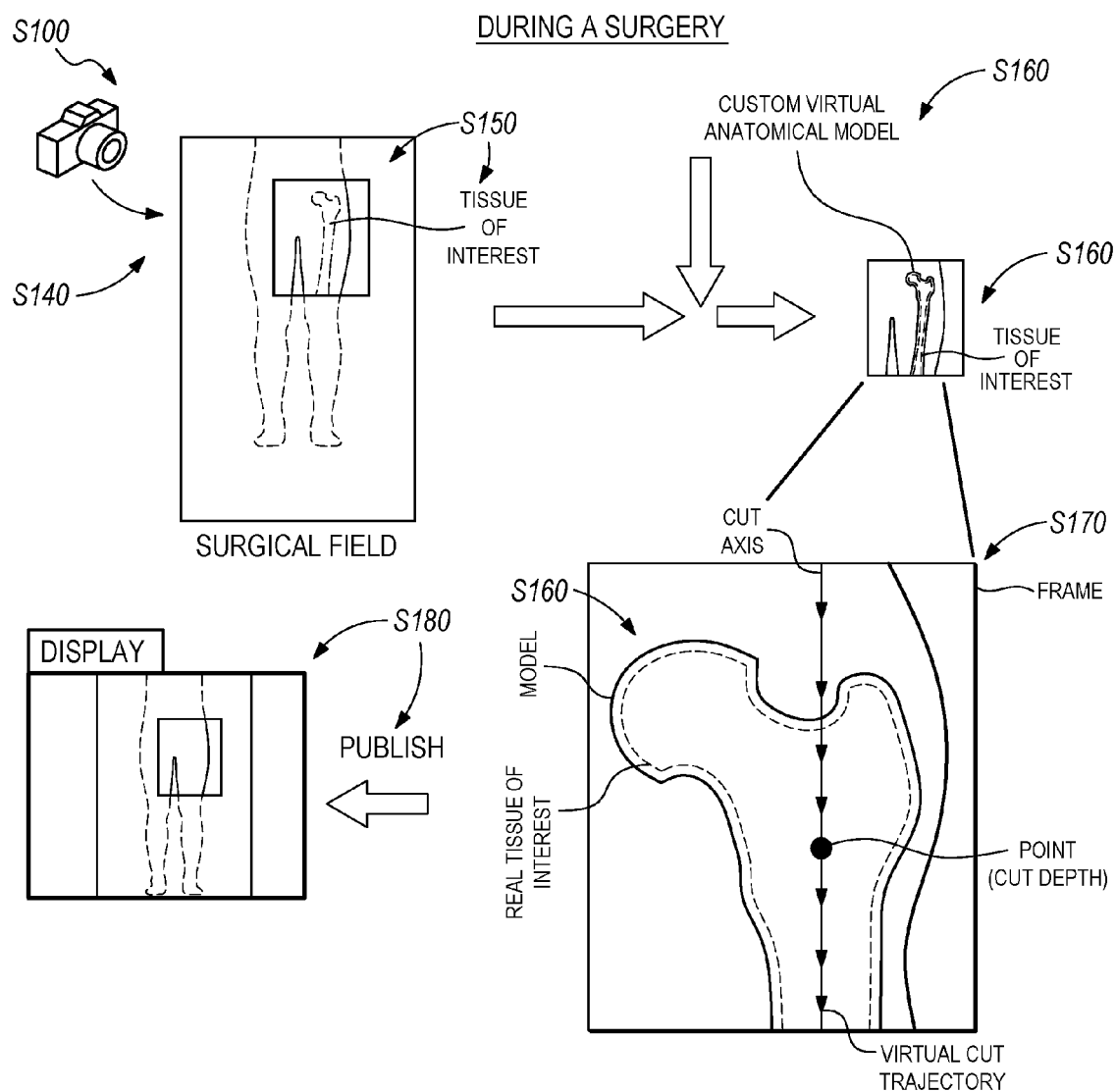

As shown in FIGS. 1, 3A and 3B, a first method S100 for augmenting a surgical field with virtual guidance content includes: accessing a scan representing a tissue of interest of a patient in Block S105; combining the scan with a generic virtual anatomical model to define a custom virtual anatomical model of the tissue of interest in Block S110; accessing a virtual model of a surgical implant in Block S115; locating the virtual model of the surgical implant within the custom virtual anatomical model in Block S120; defining a cut trajectory along a boundary of an intersection between the virtual model of the surgical implant and the custom virtual anatomical model of the tissue of interest in Block S125; aligning a virtual cut surface, defined by a virtual surgical guide, to the cut trajectory to locate the virtual model of the surgical guide relative to the custom virtual anatomical model in Block S130; during a surgical operation on the tissue of interest of the patient: at a first time, accessing an image of a surgical field captured by a sensor (e.g., an optical sensor) coupled to a computing device in the surgical field in Block S140; detecting the tissue of interest in the image in Block S150; aligning the custom virtual anatomical model to the tissue of interest detected in the image in Block S160; defining a target real location for a real surgical guide in the surgical field based on a virtual location of the virtual surgical guide aligned to the custom virtual anatomical model, the real surgical guide represented by the virtual surgical guide in Block S170; generating a frame depicting the target real location of the surgical guide in the surgical field in Block S180; and, at approximately the first time, publishing the frame depicting the target real location of the surgical guide in the surgical field in Block S190.

As shown in FIGS. 1, 3A, and 3B, one variation of the first method S100 further includes: at a second time, in response to an input to the computing device, relocating the virtual location of the virtual surgical guide to a second virtual location; aligning a second virtual cut surface to the virtual surgical guide in the second virtual location, the second virtual cut surface corresponding to the cut surface of the surgical tool; defining a second target real location for the real surgical guide in the surgical field based on the second virtual location of the virtual surgical guide; generating a second frame depicting the second target real location of the surgical guide in the surgical field; and, at approximately the second time, publishing the second frame depicting the second target real location of the surgical guide in the surgical field overlaid on the image of the surgical field.

Figure 2:
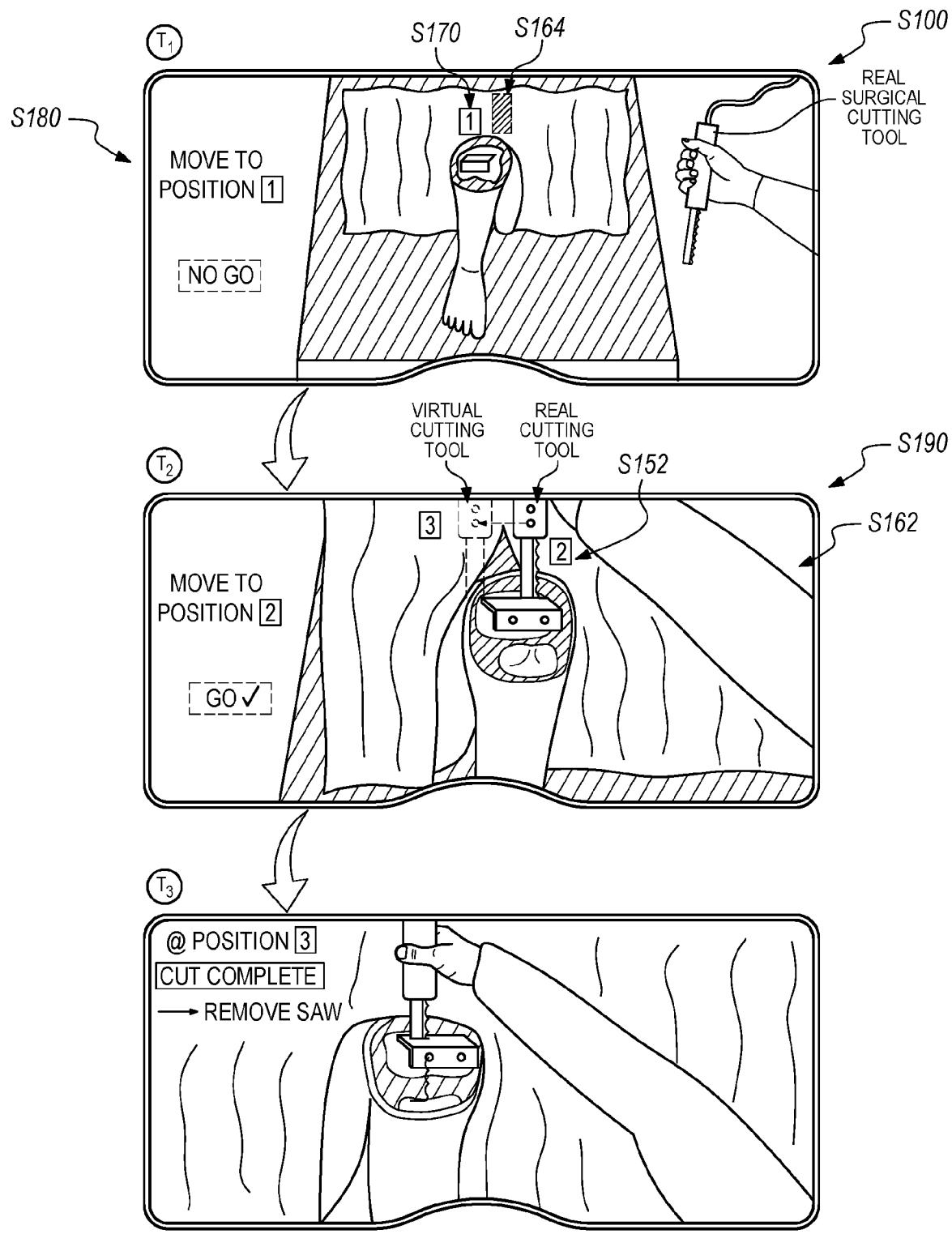
FIG. 2 is a flowchart representation of one variation of the first method.

As shown in FIG. 2, one variation of the first method S100 includes: retrieving a virtual tool model representing a real surgical tool in Block S114; accessing an image of a surgical field in Block S140; identifying a tissue of interest in the image in Block S150; virtually locating the virtual tool model to the tissue of interest within a virtual surgical environment based on a predefined surgical plan in Block S184; at a first time, generating a first augmented reality frame representing a first target position of the virtual tool model within the virtual surgical environment based on a current position of an augmented reality headset relative to the real tissue of interest in the real surgical field in Block S190; publishing the first augmented reality frame to the augmented reality headset in Block S180; tracking a position of the real surgical tool within the real surgical field environment in Block S190; at a second time, generating a second augmented reality frame representing a second target position of the virtual tool model within the virtual surgical environment based on a current position of the augmented reality headset relative to the real tissue of interest and a current position of the real surgical tool in the real surgical field in Block S170; publishing the second augmented reality frame to the augmented reality headset in Block S180.

1.1 Applications

Generally, a computer system can execute Blocks of the first method S100: to generate a sequence of augmented reality ("AR") frames containing a virtual surgical guide and depicting a surgeon's field of view—a surgical field—or a selected perspective through an AR headset, AR glasses, another AR device, and/or a display (in the surgical field or remote from the surgical field). The virtual surgical guide can be oriented from a perspective of the surgeon viewing a real human feature—a tissue of interest—within the surgical field environment. The computer system can present these AR frames to the surgeon through an AR device substantially in real-time, thereby guiding placement of a real surgical guide in the real surgical field and, thus, guiding the surgeon's application of real tools within the real surgical environment with virtual AR objects cooperating with real surgical guides, jigs, and fixtures within the real surgical field. In particular, a computer system can implement Blocks of the first method S100 to preplan a surgical operation and aid a surgeon in following this surgical plan. Thus, the computer system can implement Blocks of the first method S100 to form an AR frame by projecting a virtual surgical guide and a virtual surgical environment onto the surgeon's current field of view, the virtual surgical guide dictating a real location for a real surgical guide in the real surgical field; to serve the AR frame to an AR device worn by the surgeon substantially in real-time in order to guide the surgeon's placement of a surgical guide and, thus, use of a surgical tool within the surgical field; and to repeat this process throughout a surgery to serve updated AR frames to the surgeon substantially in real-time as the surgeon moves relative to the surgical field and to the tissue of interest of the patient and as the surgeon completes various stages of the surgery. The computer system can execute Blocks S105 through S130 of the first method S100 prior to a surgical operation to pre-plan the surgical operation; and can execute Blocks S105 through S130 of the first method S100 substantially in real-time during the surgical operation to aid in following a surgical plan.

In one example, the computer system can execute Block S110 and Block S170 to generate an AR guide frame depicting a virtual representation of a real surgical cutting guide overlaid on an image of a patient's real body part from a surgeon's perspective of the surgical field. Thus, the AR guide frame can facilitate placement of the real surgical cutting guide. The computer system can additionally execute Block S162 to generate AR frames including a virtual surgical reference, such as a virtual cutting plane, virtual cutting trajectory, or a virtual cutting axis, that indicates preferred or target placement of a blade or other surgical cutting surface within a surgical field for the surgeon's current field of view. The computing device can also execute Blocks of the first method S100 to generate AR frames including a virtual surgical tool, such as a virtual bone saw or a virtual bone drill, that indicates preferred or target placement of a real surgical tool within a surgical field for the surgeon's current field of view.

Figure 11A:
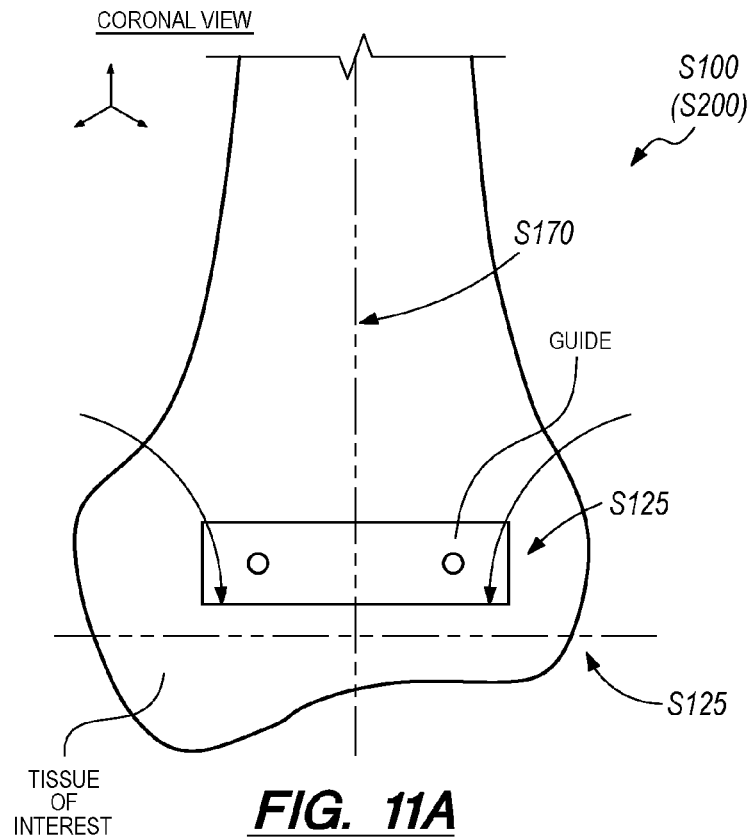
FIGS. 11A, 11B, and 11C are schematic representations of the first method.
Figure 11B:
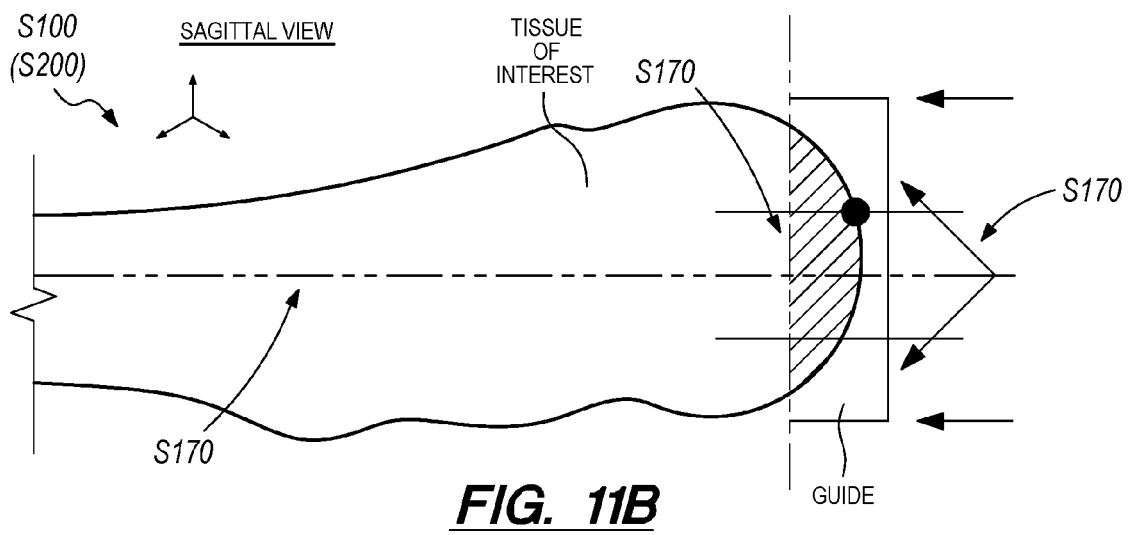
Figure 11C:
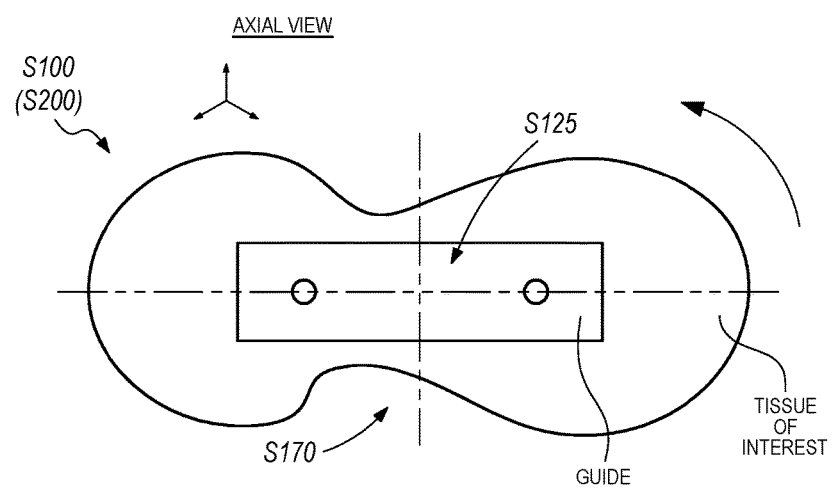

In one example application of the first method S100, prior to a knee replacement surgery, a patient undergoes a series of imaging scans, such as orthogonal radiographs or X-rays, a magnetic resonance imaging (MRI) scan, or a computerized axial tomography (CAT) scan, focusing on the knee and a section surrounding the knee (e.g., a femur and a tibia). A computer can implement Blocks of the first method S100 to develop a virtual model of the patient's knee and, generally, develop a surgical plan for replacing the knee with a surgical implant. The computer system can aggregate data from the imaging scans with a generic virtual model of a human anatomy to create a custom (patient-specific) virtual model of the patient's knee. Based on the custom virtual model, the computer system can import a virtual model of an artificial knee implant to approximate where the implant will intersect with bone—the femur and the tibia—of the patient. From this information, the surgeon (and/or the computer system) can define a surgical plan for the knee replacement surgery. In the surgical plan, the surgeon (and/or the computer system) can identify a planned cut trajectory based on the (custom) virtual model of the knee. In this example, the planned cut trajectory can include a drilled-out bore into the femur parallel a central axis of the femur to accept an artificial femoral implant. A second planned cut trajectory can remove a portion of the tibial plateau to accept an artificial tibial implant for knee arthroplasty. As shown in FIGS. 11A, 11B, and 11C, based on the planned cut trajectory, the surgeon (and/or the computer system) can plan a target location for a real surgical guide to ensure cuts in the surgical field follow the planned cut trajectory. In this example, during the surgery, a computer, such as an AR headset, can generate a guide frame indicating the target location of the real surgical guide in the (real) surgical field. The surgeon, wearing the AR headset, can see the target location overlaid on the (real) surgical field and an image of the patient in the surgical field through the AR headset's display. Thus, as the surgeon places the real surgical guide in the surgical field, the AR headset can provide real-time feedback to the surgeon indicating the proximity of the real surgical guide to the target location. Furthermore, during the surgery, the surgeon—or a surgeon remote from the surgical field—may wish to relocate the real surgical guide or follow a different cut trajectory than the planned cut trajectory. Thus, the surgeon—or a surgeon remote from the surgical field—can update, in real-time, the planned cut trajectory and the computer system can implement Blocks of the first method S100 to generate a new location for the real surgical guide; to generate a new guide frame identifying the new location in the surgical field; and to render the new guide frame in the AR headset to facilitate relocation of the real surgical guide in the surgical field.

Blocks of the first method S100 and subsequent methods can be executed locally and/or remotely, such as by a local computing device within an operating room or within a hospital, by a remote computing device (e.g., a remote server), and/or by a distributed computer network, etc. Blocks of the first method S100 can additionally or alternatively be executed by an AR headset, AR glasses, or other AR device. A device executing Blocks of the first method S100 can also interface with: an AR device; one or more cameras and distance (e.g., LIDAR) sensors; sensor-enabled tools; and/or other sensors and actuators within the operating room. However, any other local, remote, or distributed computer systems—hereinafter referred to as "the computing device"—can execute Blocks of the first method S100 substantially in real-time. Blocks of the first method S100 can also be executed locally and/or remotely by a plurality of computers. For example, Blocks S120, S125, and S130 of the first method S100 can be executed at a computer system operated by a surgeon remote from the surgical field; and Block S180 can be executed at a computer system in the surgical field to render the guide frame overlaid on the surgical field and, thus, guide placement of the real surgical guide in the surgical field.

Blocks of the first method S100 are described herein in the context of a knee replacement and a hip replacement. However, Blocks of the first method S100 can be executed by a computer system to generate and serve AR frames depicting virtual surgical guides for any other surgical application, such as: a hip replacement operation; a heart valve replacement operation; a carpel tunnel release surgery; a cataract removal procedure; etc. Furthermore, Blocks of the first method S100 are described herein in the context of serving virtual guidance for placement and operation of surgical cutting guides and surgical cutting tools (e.g., a saw, a drill) during a surgery. However, Blocks of the first method S100 can be executed by a computer system to serve virtual guidance for placement of: a fastener (e.g., a surgical anchor, a fusion plate); an implant (e.g., a metal head, an acetabular component, and a plastic liner for a hip replacement); or any other tool or object within a surgical field.

The first method S100 can therefore be implemented in conjunction with an AR device and one or more sensors within a surgical field to simplify real guides, fixtures, and other surgical guides in a surgical field. For example, by simplifying real surgical guides by augmenting the real surgical guides with virtual surgical guides, the first method S100 can: reduce requirements for real surgical guides to locate real surgical tools during a surgery; reduce a cost to outfit a surgical field with such real surgical guides; simply the construction (and cost thereof) of each real surgical guide within a surgical field; reduce a number of real elements introduced into a sterile field during a surgical operation; and/or enable rapid and comprehensive modernization of surgical guides within a surgical setting by updating virtual surgical guides rather than by replacing obsolete real surgical guides with new real surgical guides.

The real surgical guide of the first method S100 can be of any shape and form factor. For example, the real surgical guide can be a cubic block or a custom (patient-specific) three-dimensional fixture (i.e., 3D-printed or CNC machined) matched to a geometry of the tissue of interest of a particular patient. The real surgical guide can also include alignment features for aligning and fixturing the tissue of interest to the real surgical guide.

In one example implementation of the first method S100, the real surgical guide can be a cubic block with an integrated load cell. The load cell can be wirelessly coupled to the computer system(s) implementing the first method S100. In this example implementation, during a total knee arthroplasty, the real surgical guide can function to balance (or substantially equilibrate) ligament tension of ligaments affected by the total knee arthroplasty by recording tensile loads between the load cell and the ligament and transmitting the tension of each ligament to the computer system. The computer system can then publish the tension of each ligament to the display rendering the guide frame thereby informing a surgeon of a ligament tension balance or imbalance. Thus, the real surgical guide can cooperate with the computer system to provide metrics for facilitating consistent execution of a surgical plan.

1.2 Surgical Plan

In one variation of the first method S100, the computer system can access a scan representing a tissue of interest of a patient in Block S105; combine the scan with a generic virtual anatomical model to define a custom virtual anatomical model of the tissue of interest in Block S110; access a virtual model of a surgical implant in Block S115; locate the virtual model of the surgical implant within the custom virtual anatomical model in Block S120; define a cut trajectory along a boundary of an intersection between the virtual model of the surgical implant and the custom virtual anatomical model of the tissue of interest in Block S125; and align a virtual cut surface, defined by a virtual surgical guide, to the cut trajectory to locate the virtual model of the surgical guide relative to the custom virtual anatomical model in Block S130. Generally, in this variation of the first method S100, the computer system can interface with a surgeon (and/or radiologist, etc.) to define a surgical plan for a patient's upcoming surgery and, from the surgical plan, define an optimal location for placement of a surgical guide in the surgical field to assist in execution of the surgical plan.

In Block S105 of the first method S100, the computer system: accesses a scan representing a tissue of interest of a patient. Generally, the computer system accesses two-dimensional ("2D") or three-dimensional ("3D") MRI, CAT, X-ray (radiograph), or other scan data of a region of a patient's body designated for an upcoming surgery.

In Block S110 of the first method S100, the computer system combines the scan with a generic virtual anatomical model to define a custom virtual anatomical model of the tissue of interest. In particular, the computer system can implement edge detection, pattern matching, object recognition, and/or any other computer vision first method S100 or technique to automatically identify discrete tissue masses—such as skin, bone, cartilage, blood vessels, lymph nodes, muscle, and/or nerve tissue—in the scan data. Based on types and relative positions of discrete tissues thus identified in the scan data, the computer system can automatically label discrete tissues within the scan data with anatomical names or other identifiers. Thus, generally, the computer system can function to convert a generic virtual anatomical model into a patient-specific model (represented by the custom virtual anatomical model).

In one example of Block S110 of the first method S100, for a surgeon preparing for a total knee replacement in a patient's right knee, the computer system can: access a 3D MRI scan of the patient's right leg from approximately eight inches below the tibial condyle to approximately eight inches above the femoral condyle, and transform this 3D MRI scan into a 3D point cloud, wherein each point in the 3D point cloud is labeled with a tissue density from a corresponding region of the 3D MRI scan. The computer system can then identify clusters of points with like tissue density labels in the 3D point cloud, identify boundaries between distinct clusters of points with like tissue density labels, and group contiguous clusters of points with like tissue density labels as discrete tissue masses in the 3D point cloud. The computer system can also implement known tissue density ranges for various types of tissue—such as a tissue density range for each of skin, bone, cartilage, blood vessels, lymph nodes, muscle, and/or nerve tissue—to label each point of a discrete tissue mass in the 3D point cloud with a particular tissue type. The computer system can then: retrieve a generic virtual anatomical model of a right leg, including anatomical tissue labels; globally and/or locally scale, articulate, rotate, translate, or otherwise manipulate the virtual leg model to approximately align discrete virtual tissues in the virtual leg model with discrete tissue masses of similar tissue densities, types, geometries, and/or relative positions (e.g., relative to other tissue types) in the 3D point cloud; and transfer anatomical tissue labels from the virtual leg model to the 3D point cloud.

Alternatively, the computer system can implement template matching techniques to match template tissue point clouds—labeled with one or more anatomical tissue labels—to tissue masses identified in the 3D point cloud and transfer anatomical tissue labels from matched template tissue point clouds to corresponding tissue masses in the 3D point cloud. Yet alternatively, the computer system can: implement computer vision techniques, such as edge detection or object recognition, to automatically detect distinct tissue masses in the scan data; present these distinct tissue masses in the scan data to the surgeon through the surgeon portal; and write an anatomical tissue label to each distinct tissue mass in the 3D point cloud based on anatomical tissue labels manually entered or selected by the surgeon through the surgeon portal. However, the computer system can implement any other method or technique to label tissues within patient scan data automatically or with guidance from a surgeon.

In one variation, the computer system can scale, articulate, translate, rotate, or otherwise manipulate virtual tissue objects within a generic virtual anatomical model (or generic virtual tissue model) of a similar region of a human body into alignment with corresponding labeled tissue masses in the 3D point cloud, as shown in FIG. 1. For example, the computer system can: locally scale and reorient surfaces of a generic virtual tibia to mimic the geometry of a tibia labeled in the 3D point cloud; locally scale and reorient surfaces of a generic virtual quadriceps muscle to mimic the geometry of a quadriceps muscle labeled in the 3D point cloud; locally scale and reorient surfaces of a generic virtual iliotibial band to mimic the geometry of a iliotibial band labeled in the 3D point cloud; and locally scale and reorient generic virtual skin—around the virtual customized tibia, the virtual customized quadriceps muscle, and the virtual customized iliotibial band—to mimic the geometry of the exterior of the patient's leg shown in the 3D point cloud. The computer system can thus generate a patient-specific virtual tissue model of a region of the patient's body scheduled for surgery by merging real patient scan data with a generic virtual anatomical model of a human body or region of a human body.

In one example application of the first method S100, the computer system can combine orthogonal X-ray radiographs of a patient with a generic (parameterized) anatomical virtual model of a human anatomy. In order to yield a custom (patient-specific) virtual anatomical model reflective of the patient's anatomy, the computer system can extract a first point from the set of orthogonal radiographs corresponding to a first discrete location of the tissue of interest and query the generic virtual anatomical model for a first virtual point in the generic virtual anatomical model corresponding to the first point from the set of orthogonal radiographs. The first virtual point can be located in the generic virtual anatomical model by pattern matching the orthogonal radiographs with the generic virtual anatomical model to find similar geometry patterns (and shapes). In this example, the first point can be aligned adjacent a tibial plateau of the patient's tibia. The computer system can identify a shape of the tibial plateau in the orthogonal radiographs by matching a similar shape of a tibial plateau in the generic anatomical model. The computer system can then locate the first virtual point relative to geometric features of the tibia in the generic virtual model by identifying proximity of the first point to geometric features of the tibia in the orthogonal radiographs. The computer system can further extract a second point from the set of orthogonal radiographs corresponding to a discrete location of the tissue of interest; and define a second virtual point in the generic virtual anatomical model corresponding to the second point from the set of orthogonal radiographs. Based on a distance between the first and second points in the orthogonal radiographs, the computer system can scale the generic virtual anatomical model to define the custom virtual anatomical model by scaling a virtual distance between the first virtual point and the second virtual point in the custom virtual anatomical model to correspond to the real distance between the first point and the second point in the set of orthogonal scans. Thus, a virtual distance between the first virtual point and the second virtual point can be proportional to the real distance in the set of orthogonal scans.

In another implementation, the computer system can also detect a mechanical axis of the tissue of interest in the scan and distort the generic virtual anatomical model of the tissue of interest into alignment with the scan to define the custom virtual anatomical model by aligning a mechanical axis of the generic virtual anatomical model with the mechanical axis of the tissue of interest. For example, the computer system can locate a center of a femoral head of a femur and a midpoint of an ankle in a MRI scan and define a mechanical axis between the center of the femoral head and the midpoint of the ankle. The computer system can then locate a center of a generic femoral head of a femur and a center of a generic midpoint of an ankle in the generic virtual anatomical model to define a virtual mechanical axis between the center of the generic femoral head and the center of the generic midpoint of an ankle. To combine the scan with the generic virtual anatomical model, the computer system can align the virtual mechanical axis with the mechanical axis of the tissue of interest. The computer system can also append (or regenerate) the frame to include positional guides in Block S180, identifying degrees of varus angulation, valgus angulation, flexion, and extension of the tissue of interest relative to the mechanical axis of the tissue of interest. For example, in a normal lower extremity limb, the (normal) mechanical axis of the tissue of interest, identified by drawing an axis from the center of the femoral head to the midpoint of the ankle, can align with the medial tibial spine. A lower extremity limb with valgus angulation (bow legs) or varus angulation (X legs) can have mechanical axes—identified by drawing an axis from the center of the femoral head to the midpoint of the ankle)—with pass through a point adjacent the knee distinct from the medial tibial spine.

As shown in FIG. 3A, the computer system can implement Blocks S115 and S120 of the first method S100 accessing a virtual model of a surgical implant in Block S115 and locating the virtual model of the surgical implant within the custom virtual anatomical model in Block S120. Generally, once the patient scan data is thus transformed into a (patient-specific) custom virtual anatomical tissue model, the computer system can automatically retrieve virtual models of one or more implanted devices, surgical tools, surgical guides, surgical fasteners, etc., and place these within the patient-specific virtual tissue model (or within the 3D point cloud, or within the 3D scan data, etc.) based on a type of surgery selected by the surgeon. In the foregoing example in which the surgery is a total knee replacement, the computer system can retrieve virtual models for an artificial femoral component, an artificial tibial component, an artificial patellar component, a femoral cutoff guide, and/or a tibial cutoff guide. In this example, the computer system can then automatically place the components in target implant positions within the patient-specific virtual tissue model based on locations within the patient-specific virtual tissue model. The computer system can then serve the patient-specific virtual tissue model with the components positioned accordingly in the patient-specific virtual tissue model to the surgeon through the surgeon portal. The computer system can also determine target positions of the femoral and tibial cutoff guides relative to the femur and tibia in the patient-specific virtual tissue model to achieve these initial artificial femoral, tibial, and patellar component positions; and the computer system can serve the patient-specific virtual tissue model to the surgeon through the surgeon portal, as shown in FIG. 1.

From the patient-specific custom virtual anatomical model including the surgical implant, the computer system defines a cut trajectory along a boundary of an intersection between the virtual model of the surgical implant and the custom virtual anatomical model of the tissue of interest in Block S125. Generally, the computer system can retrieve the custom virtual anatomical model—corresponding to a patient—with an integrated virtual model of the surgical implant of Blocks S115 and S120, and define a cut trajectory along the intersection of the virtual model of the surgical implant and the custom virtual anatomical model of the tissue of interest. In one implementation of Blocks S125, the computer system can interface with a surgeon (i.e., through a surgeon portal) to define a planned virtual cut trajectory roughly aligned with the intersection of the virtual model of the surgical implant with the custom anatomical model. In this implementation the surgeon can define a virtual cut trajectory, intersecting with the tissue of interest in the custom virtual anatomical model, of any shape and depth. For example, the virtual cut trajectory can be a cut plane, traversing the tissue of interest, a drilled bore aligned with an axis of the tissue of interest, a 3D cut surface, or any other cut geometry. In one example implementation, the computer system can then serve the patient-specific virtual tissue model to the surgeon and then interface with the surgeon to locate a surgical jog model, a virtual cut plane, a cutting tool trajectory, and/or any other virtual surgical object relative to these discrete tissues to define a surgical plan for the upcoming surgery.

Alternatively, in another implementation of Block S125, the computer system can define target positions of cut planes relative to the femur and tibia in the patient-specific virtual tissue model to achieve sufficient bone removal for the target artificial femoral, tibial, and patellar component positions, as shown in FIG. 1. The computer system can similarly define cutting tool trajectories (e.g., "cut paths") in the patient-specific virtual tissue model that, when executed with a real surgical saw, yield sufficient bone removal to achieve the foregoing component positions. The computer system can thus serve the patient-specific virtual tissue model—with the virtual cut planes and/or with a virtual cutting tool animated along the cutting tool trajectories in the patient-specific virtual tissue model—to the surgeon through the surgeon portal. The surgeon can then accept or modify these target positions of the artificial femoral component, the artificial tibial component, the artificial patellar component, the cut planes, and/or the cutting tool trajectories through the surgeon portal. The computer system can thus automatically construct a virtual surgical environment depicting virtual patient tissue and locating one or more virtual surgical objects relative to the virtual patient tissue.

Alternatively, the computer system can define the cut trajectory relative to the tissue of interest as: a cut axis depicted as a line in the (virtual) guide frame defining a direction of the cut trajectory relative to the custom virtual anatomical model; and a cut depth depicted as a point in the guide frame defining a depth of a cut surface relative to the custom virtual anatomical model. The computer system can then generate the guide frame in Block S170 including the cut axis (line) and cut depth (point) overlaid on the image of the surgical field, such as by projecting the line and the point onto a field of view of a surgeon—in the surgical field—wearing an AR headset.

Alternatively, the computer system can interface with the surgeon through the surgeon portal to: manually identify discrete tissues in patient scan data; align—manually or automatically—a generic virtual anatomical model to patient scan data; locate one or more virtual implants, surgical tools, surgical guides, surgical fasteners, etc. relative to the patient's scan data or relative to an object in a patient-specific virtual tissue model; and/or define a cut plane or a cutting tool trajectory for an upcoming surgery.

The computer system can thus construct a virtual surgical environment depicting both patient tissue and one or more virtual surgical objects based on data entered by a surgeon, radiologist, etc. However, the computer system can implement any other method or technique to automatically—or with guidance from one or more surgeons, radiologists, nurses, etc.—generate a virtual 3D (or 2D, or 4D) model defining a surgical plan for an upcoming surgery.

In one variation of Blocks S115 and S120 of the first method S100, the virtual model of the surgical implant can include recommended cutting and alignment information for the surgical implant. For example, the virtual model of Block S125 can be a 3D representation of the surgical implant in which, when integrated with the custom virtual anatomical model of Blocks S115 and S120, the custom virtual anatomical model can reflect a recommended cut surface finish (e.g., optimized for adhesion of bone cement) of a recommended surgical tool and a recommended surgical cut contour specified with the virtual model of the surgical implant. The virtual model of the surgical implant can also include recommended cut geometries and depth, ideal alignment, screw and pin dimensions, and other surgical information to generate a realistic model of a human anatomy after implantation of the surgical implant.

Block S130 of the first method S100 recites aligning a virtual cut surface, defined by a virtual surgical guide, to the cut trajectory to locate the virtual model of the surgical guide relative to the custom virtual anatomical model. Generally, the computer system can define a location for a virtual model of a surgical guide that corresponds to—and facilitates—the cut trajectory defined in Block S125. The surgical guide can be of any shape or size, can be of a generalized form factor for different tissue types and patients, or can be customized to a patient and/or to a particular tissue of the patient. In one implementation of Block S130, the virtual model of the surgical guide can be arranged adjacent the virtual cut trajectory in the custom virtual anatomical model. Thus, the surgical guide can function to virtually guide a cutting tool along the virtual cut trajectory. The computer system can simulate the virtual cut trajectory of a virtual surgical tool resulting from placement of the virtual surgical guide in the custom virtual anatomical model.

1.3 Image of the Surgical Field

Block S140 of the first method S100 recites, during a surgical operation on the tissue of interest of the patient, at a first time, accessing an image of a surgical field captured by a sensor coupled to a computing device in the surgical field. Generally, in Block S140, the computer system interfaces with one or more cameras or other sensors to collect images of a surgical field. For example, the computer system can download digital photographic color images from a forward-facing camera or optical sensor arranged on each side of an AR headset worn by a surgeon during the surgery. In another example, the computer system can download digital photographic color images from multiple downward-facing cameras arranged in a fixed location over an operating table within an operating room. In these examples, the computer system (or a remote computer contracted by the computer system) can stitch images captured substantially simultaneously by two or more cameras within the operating room into a 3D point cloud or other 3D image of a volume within the operating room (hereinafter "3D surgical field image").

The computer system can additionally or alternatively download distance data, such as in the form of a 3D point cloud output by a LIDAR sensor arranged over the operating table. The computer system can further merge digital photographic color images with distance data to generate a substantially dimensionally-accurate color map of a volume within the operating room.

The computer system can collect these one or more images in Block S140 and process these images as described below substantially in real-time. The computer system can collect images from one or more cameras—in fixed locations or mobile within the surgical field—or distance data from one or more other sensors at a frame rate similar to a projection frame rate of the AR device, such as thirty frames per second. However, the computer system can collect any other color, distance, or additional data from any other type of sensor throughout a surgery.

1.4 Virtual Surgical Object Location

Block S150 of the first method S100 recites detecting the tissue of interest in the image; Block S160 recites aligning the custom virtual anatomical model to the tissue of interest detected in the image; and Block S170 of the first method S100 recites defining a target real location for a real surgical guide in the surgical field based on a virtual location of the virtual surgical guide aligned to the custom virtual anatomical model, the real surgical guide represented by the virtual surgical guide. In one implementation of the first method S100, the computer system locates virtual surgical objects (e.g., a virtual surgical guide, virtual surgical jig, a cut plane, a virtual surgical tool, etc.) in a patient-specific virtual tissue model generated by merging a generic virtual anatomical model with patient scan data, as described above. In this implementation, the computer system can process the 3D surgical field image to identify a human feature in the real surgical field in Block S150 and can then align the patient-specific virtual tissue model to the human feature within the virtual surgical environment in Block S160. Because the virtual surgical object is located by the patient-specific virtual tissue model, the computer system can thus locate the virtual surgical guide and other virtual surgical objects within the virtual surgical environment. By thus mapping a patient-specific custom virtual tissue model within the virtual surgical environment onto real patient tissue identified in the 3D surgical field image in Block S150, the computer system can later generate an AR frame containing virtual content aligned to real patient tissue in the surgical field in Blocks S180 and S190, such as by projecting the virtual surgical environment onto the surgeon's known or calculated field of view, as described below.

In one example in which a patient's right knee is undergoing a total knee replacement, the computer system can: transform 2D images captured by cameras within the operating room into a 3D surgical field image in Block S140; identify the patient's right leg in the 3D surgical field image in Block 150; and map a (patient-specific) custom virtual knee model of the patient's right leg onto the patient's right leg in the 3D surgical field image to define (e.g., orient) the patient-specific virtual knee model in the virtual surgical environment in Block S160. In this example, the computer system can implement object detection, edge detection, surface detection, and/or any other computer vision technique to distinguish distinct volumes or surfaces in the 3D surgical field image; the computer system can then compare a patient-specific virtual tibia model—within the patient-specific virtual knee model of the patient's greater right leg—to these distinct volumes or surfaces in the 3D surgical field image to identify the patient's lower right leg represented in the 3D surgical field image. Similarly, the computer system can compare a patient-specific virtual femur model—within the patient-specific virtual tissue model of the patient's greater right leg—to these distinct volumes or surfaces in the 3D surgical field image to identify the patient's right thigh represented in the 3D surgical field image. By separately scaling, rotating, and translating the patient-specific virtual tibia model and the patient-specific virtual femur model into alignment with like volumes or surfaces in the 3D surgical field image, the computer system can locate and align each side of a virtual articulable knee joint model in the virtual surgical environment to the real position of the patient's right leg in the surgical field in Block S140.

In the foregoing implementation, the computer system can compare various tissue types in the virtual patient-specific tissue model and in the 3D surgical field image to align the virtual patient-specific tissue model to the 3D surgical field image in Block S160. In particular, the computer system can implement edge detection, color matching, texture recognition, and/or other computer vision techniques to distinguish skin, muscle, bone, and other tissue in the 3D surgical field image. For example, the computer system can: associate a smooth, non-geometric surface with skin; associate a rough red surface inset from a skin surface with muscle; and associate a smooth, light pink or (near-) white surface inset from both skin and muscle surfaces as bone. The computer system can then label points or surfaces in the 3D surgical field image accordingly and scale, translate, rotate, and/or otherwise manipulate virtual surfaces or virtual volumes in the patient-specific knee model into alignment with corresponding labeled surfaces in the patient-specific knee model. The computer system can therefore detect different types of tissue within the surgical field and dynamically map a virtual patient-specific tissue model to one or more tissue types throughout a surgery as the patient's body is manipulated and as different tissues are exposed.

Alternatively, the computer system can align patient scan data (rather than the patient-specific tissue model) to a tissue of interest identified in the 3D surgical field image and can locate 3D patient scan data within the virtual surgical environment according to the position of the tissue of interest in the surgical field.

In the foregoing implementations, a reference marker of known dimension is placed in the field of the scanner when the MRI, CAT, X-ray, or other scan data of the region of the patient's body is recorded. For example, three 1"-diameter steel spheres can be placed at different (X, Y, Z) positions around a patient's right knee when the patient's right knee is imaged in an MRI scanner. When analyzing an MRI scan in Block S210 to generate a surgical plan, the computer system can interpolate real dimensions of the patient's tissues (e.g., general and feature-specific length, width, depth of the tibia, femur, patella, tibial condyle, and femoral condyle, etc.) based on known dimensions of the reference marker(s). The computer system can label regions of patient tissues with these dimensions and/or can scale or modify generic virtual anatomical models into alignment with these dimensions extracted from the patient scan data. For example, the virtual tissue models can be parameterized, and the computer system can pass dimensions extracted from the patient scan data into parameterized virtual tissue models to generate patient-specific virtual tissue models. The computer system can then define a surgical plan—including quantitative positions of an implant device or cut plane, etc. relative to reference tissues (e.g., the patient's bones)—from these patient-specific virtual tissue models. Furthermore, the computer system can later compare these dimensions extracted from patient scan data to calculate dimensional differences between target surgical operations defined in the surgical plan and actual surgical operations completed during the subsequent surgery.

The computer system can also identify and characterize (e.g., dimension) substantially unique tissue features within the patient's scan data. For example, for scan data of a patient designated for an upcoming hip surgery, the computer system can characterize the size and geometry of the cotyloid fossa of the patient's acetabulum and then reference surgical operations on the patient's hip in the surgical plan to these unique features of the patient's cotyloid fossa. Later, during the operation, the computer system can: detect such features on the patient's cotyloid fossa in a feed of images of the surgical field when the patient's hip is opened and the cotyloid fossa exposed; orient a virtual acetabulum model to the cotyloid fossa shown in the image feed; and calculate quantitative differences (e.g., dimensional deviations) between target operations on the hip defined in the surgical plan and real operations performed on the hip relative to the patient's cotyloid fossa identified in the image feed. Therefore, in addition to scaling a generic virtual anatomical model to the patient's skeletal structure measured from scan data, the computer system can also redefine virtual surfaces within a patient-specific virtual tissue model according to unique tissue features identified in X-ray, MRI, CAT, and/or other scan data of the patient.

In one example implementation of the first method S100, the computer system can sequentially detect, in the image, the surgical field, the patient, and a section of the patient including a soft tissue component including vascular features, neuromuscular components, etc. surrounding the tissue of interest. Alternatively, the computer system can selectively detect objects in the image of the surgical field in any order.

The computer system can then retrieve a virtual guide model representing a real surgical guide—such as from a virtual model database or from the surgical plan—in Block S110 and locate the virtual guide model relative to the patient-specific virtual tissue model within the virtual surgical environment based on guide position definitions in the surgical plan. For example, the surgical plan can specify: a tibial cutoff guide (e.g., in the form of a pointer to a virtual tibial cutoff guide) and a location and orientation of the tibial cutoff guide relative to the patient's tibial condyle; and a femoral cutoff guide and a location and orientation of the femoral cutoff guide relative to the patient's femoral condyle. The computer system can thus separately locate a virtual tibial cutoff guide model relative to a virtual tibial condyle in the virtual surgical environment and locate a virtual femoral cutoff guide model relative to a virtual femoral condyle in the virtual surgical environment based on these location and orientation definitions in the surgical plan.

The surgical plan can similarly define positions of a virtual cut plane, a virtual cut axis, a virtual surgical tool, a virtual surgical tool trajectory, and/or any other virtual surgical object relative to the patient-specific virtual tissue model. The computer system can therefore implement methods and techniques as described above: to locate a virtual cut plane within the virtual surgical environment in Block S162; to locate a virtual surgical tool within the virtual surgical environment in Block S184; or to locate any other virtual surgical object within the virtual surgical environment.

However, the computer system can implement any other method or technique to detect a surface or volume corresponding to a region of a patient's body in Block S150, to align scan data or a virtual tissue model to the region of a patient's body in the real surgical environment in Block S160, and to locate a target real location of a real surgical guide within the surgical environment in Blocks S160, S162, and/or S164. The computer system can repeat the foregoing process for each image retrieved in Block S140 substantially in real-time to update positions of the virtual tissue model and virtual surgical guides within the virtual surgical environment, such as at a rate of thirty frames per second, throughout the surgery.

1.5 Augmented Reality Frame

Block S170 of the first method S100 recites generating a frame depicting the target real location of the surgical guide in the surgical field; and Block S180 of the first method S100 recites, at approximately the first time, publishing the frame depicting the target real location of the surgical guide in the surgical field. Generally, in Block S170, the computer system transforms locations of virtual surgical objects (a virtual guide, the virtual cut plane, and/or the virtual surgical tool) in a current instance of the virtual surgical environment into a 2D or 3D AR guide frame, indicating target locations of real surgical objects in the surgical field, based on the surgeon's current field of view of the surgical field. The computer system can then serve the AR frame to the surgeon via the AR device in Block S180, thereby supplementing the surgeon's field of view with virtual guides aligned to real guides in the surgical field.

In one implementation in which the computer system retrieves images recorded by cameras (e.g., integrated into the AR device at fixed positions and orientations relative to a lens or visor in the AR device), the computer system implements a static transform—corresponding to these known relative positions and orientations of the cameras—to project the virtual surgical environment (or one or more virtual surgical objects within the virtual surgical environment) onto the surgeon's field of view, as shown in FIG. 1. In this implementation, by aligning virtual objects in the virtual surgical environment to real objects represented in images recorded by cameras in the AR device in Block S140, the computer system thus aligns the virtual surgical environment to the field of view of these cameras. Furthermore, because these cameras are fixed in the AR device at known positions and orientations relative to a lens or visor in the AR device, the computer system can implement a static transform to capture a 2D or 3D perspective of the virtual surgical environment aligned to the surgeon's field of view. The computer system can thus generate a 2D or 3D AR frame showing the virtual guide model from this 2D or 3D perspective of the virtual surgical environment in Block S180 and, therefore, indicate a target location for the surgical guide in the surgical field.

In another implementation in which the computer system retrieves images recorded by cameras physically disconnected from the AR device, the computer system can calculate a transform for the current virtual surgical environment based on a current position of the AR device (or a lens or visor in the AR device) relative to the cameras before applying this transform to the virtual surgical environment to generate an AR frame. For example, the computer system can implement object recognition techniques to identify the AR device (or the surgeon's eyes, etc.) in a current image of the surgical field, determine the relative position and orientation of the AR device (or the surgeon's eyes, etc.) in the surgical field, and calculate the transform accordingly. Thus, the computer system can align an image of the surgical field to the surgeon's field of view by applying a known transform of the image of the surgical field from an augmented reality headset camera to the surgeon's eyes and rendered the transformed image through a display of the augmented reality headset. Alternatively, a surgeon can select a particular perspective of the surgical field through which the surgeon wishes to view the surgical field. For example, the surgeon may wish to view an isometric view of a femur in the surgical field. The surgeon can select an isometric perspective through a portal displayed in the augmented reality headset. In this example, the surgeon can select an origin of the isometric perspective through the portal displayed in the augmented reality headset or the origin of the isometric perspective can be pre-defined at a particular distance from the femur. Then, the computer system can align the image of the femur to a pre-defined isometric perspective of the femur by applying a transform of the image from the origin of the isometric perspective to the surgeon's eyes. Thus, the computer system can render the image of the surgical field from any perspective.

In another example: optical fiducials can be arranged within the surgical field; cameras arranged over an operating table can serve images of the optical field to the computer system; the AR device can include an integrated camera that captures and uploads reference images to the computer system; and the computer system can transform the current image of the surgical field into a 3D surgical field image in Block S180, identify the optical fiducials in the current 3D surgical field image, identify these same optical fiducials in a current reference image received from the AR device camera at approximately the same time, match the optical fiducials in the current 3D surgical field image and the current reference image, and calculate the transform that maps the optical fiducials from the 3D surgical field image to the optical fiducials in the reference image. The computer system can then apply the transform to the current virtual surgical environment to generate a 2D or 3D AR frame substantially in real-time. However, the computer system can implement any other method or technique to generate an AR frame representing one or more virtual surgical objects in a perspective of the virtual surgical environment corresponding to the surgeon's current field of view.

In another implementation, the computer system can scale (or zoom into or out of) the image of the surgical field and the AR frame. Thus, the computer system can fit the AR frame to an aspect ratio of a display and/or zoom into the frame to ease visualization of the tissue of interest. For example, the surgeon may wish to render an overlay frame, including the target real location of the surgical guide aligned to the image of the surgical field in the surgeon's field of view, in a large display (or monitor) in a surgical observation deck outside of an operating room in which the surgeon is performing a surgical operation. By rendering the image of the surgical field in the surgical observation deck, the surgeon can portray her view of the surgical field for others—nurses, residents, students, and other surgeons—to view. To avoid distortion of the frame, the computer system can scale the frame by maintaining a known aspect ratio of the frame and resizing the frame—at the known aspect ratio—to correspond to an aspect ratio of the display.

In another implementation, the surgeon can resize a portion of the frame (i.e., zoom into or out of the frame) to improve visualization of the portion of the frame. By maintaining a known aspect ratio of the frame, the computer system can avoid distortion of the frame while resizing the frame.

The computer system can then serve the AR frame to the surgeon's AR device substantially in real-time. For example, the foregoing Blocks of the first method S100 can be executed by a local computer system, and the local computer system can upload the AR frame to the AR device over wireless communication protocol or over a wired connection. Upon receipt of the AR frame, the AR device can project the AR frame onto a lens or visor in the AR device or onto the surgeon's eye(s) for visual consumption by the surgeon substantially in real-time.

The computer system can therefore cooperate with the AR device to augment the surgeon's field of view of a real surgical field with a virtual representation of a surgical guide snapped to (e.g., located by) a tissue of interest in the surgical field. For example, as a surgeon prepares to place a real femoral cutoff guide on a patient's right femur, the computer system can generate an AR frame that—when displayed by the AR device—shows a virtual femoral cutoff guide over the patient's right femur in the surgeon's field of view. The surgeon can then align a real femoral cutoff guide with the virtual femoral cutoff guide shown in her field of view thus augmented by the AR device, thereby locating the real femoral cutoff guide according to a femoral cutoff guide position defined in the surgical plan. Furthermore, the computer system can repeat the foregoing process for each subsequent image retrieved from the camera(s) in Block S140 in order to maintain alignment of the virtual femoral cutoff guide with the real patient's leg in the surgeon's field of view in instances of AR frames displayed on the AR device as the surgeon's field of view changes relative to the patient's leg and as the patient's leg is moved.

Figure 4A:
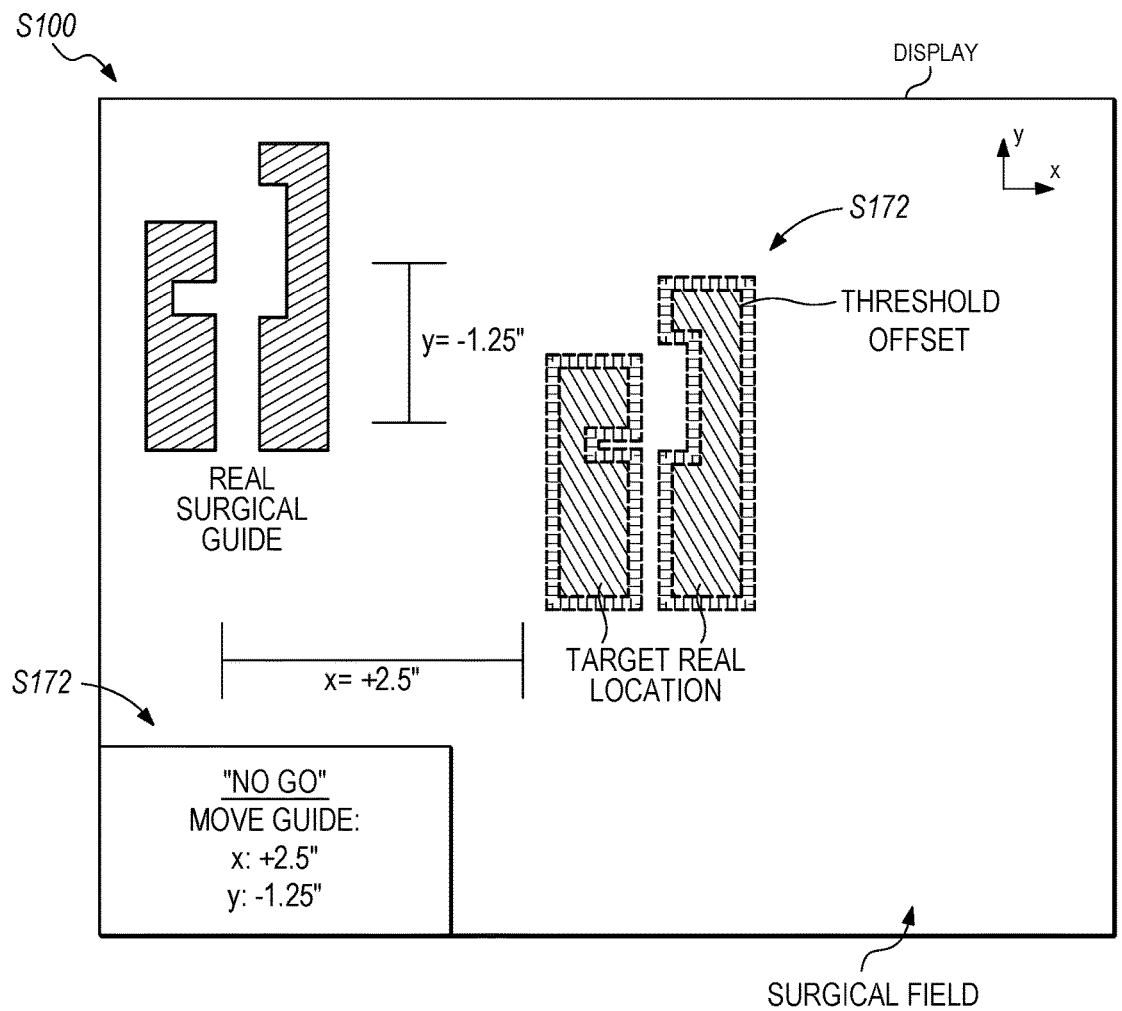
FIGS. 4A and 4B are schematic representation of the first method.

In the foregoing example, as the surgeon brings a real femoral cutoff guide into her field of view, the computer system can implement template matching and/or other computer vision techniques to identify the femoral cutoff guide in a latest image of the surgical field in Block S190, as shown in FIG. 1. For example, the computer system can retrieve a 2D template image or 3D virtual model of a femoral cutoff guide specified in the surgical plan and compare this 2D template image or 3D virtual model to the latest image of the surgical field (or a latest 3D surgical field image generated from multiple 2D images of the surgical field) to identify and track the real femoral cutoff guide in the surgical field in Block S170. Once the surgical guide is identified in the surgical field, the computer system can project the current real position of the femoral cutoff guide into the virtual surgical environment and identify a difference (e.g., angular and linear offsets along three axes) between the real position of the femoral cutoff guide and the location of the virtual femoral cutoff guide in the virtual surgical environment. If the current real position of the femoral cutoff guide (i.e., a center of the guide) differs from the target position of the femoral cutoff guide relative to the patient's femur—defined in the virtual surgical environment according to the surgical plan—by more than a threshold offset (e.g., by more than 2° about a flexion axis, by more than 1° about an internal rotation axis, by more than 0.5° about an abduction axis, or by more than 0.10" along any axis), the computer system can visually indicate this difference in a next AR frame (i.e. through a warning graphic). As shown in FIG. 4A, the computer system can also indicate a distance and direction to move the surgical guide in order that the surgical guide to be within the threshold offset (or distance) of the target position in Block S172. For example, the computer system can generate an AR frame including a virtual femoral cutoff guide in alignment with the target femoral cutoff guide location and a red translucent overlay aligned with the real femoral cutoff guide in the surgeon's field of view to indicate to the surgeon that the real femoral cutoff guide is not currently located on the patient within a threshold tolerance. The computer system can repeat this process with each subsequent image retrieved in Block S140 until the femoral cutoff guide is positioned in the surgical field relative to the patient's femur within an angular and linear tolerance of the target femoral cutoff guide location.

Figure 4B:
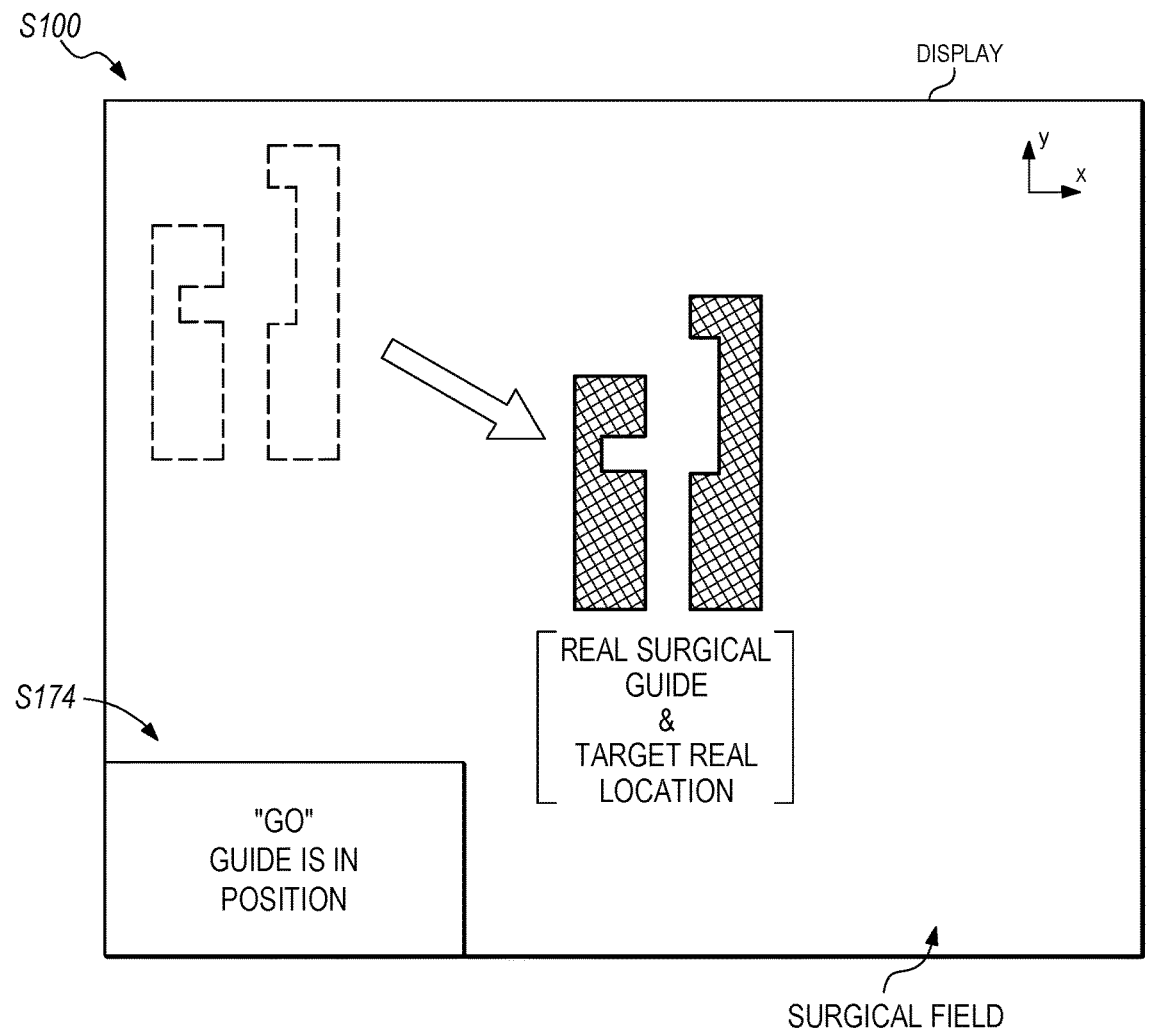

As shown in FIG. 4B, once the femoral cutoff guide is located on the patient's femur within the angular and linear tolerance of the target femoral cutoff guide location, the computer system can generate an AR frame including an approval graphic in Block S174, such as a green translucent overlay aligned with the real femoral cutoff guide in the surgeon's field of view to indicate to the surgeon that the real femoral cutoff guide is properly located on the patient within the threshold tolerance; the surgeon can then pin the real femoral cutoff guide to the patient's femur. The computer system can additionally or alternatively calculate an angular and linear offset between the real femoral cutoff guide and the target femoral cutoff guide location and populate a next AR frame with these quantitative offset values or present these values to the surgeon through another display within the operating room, as shown in FIGS. 1, 3A, and 3B. The computer system can also insert a virtual coordinate system linked to the virtual femoral cutoff guide into an AR frame and populate the virtual coordinate system with up to six arrows (e.g., three translational and three rotational arrows) indicating necessary translation and rotation of the real femoral cutoff guide to align with the target femoral cutoff guide location. However, the computer system can implement any other method or technique to identify a real femoral cutoff guide (or other real surgical object) in the field, to detect a deviation between the real position of the femoral cutoff guide and a target femoral cutoff guide location relative to a tissue of interest (e.g., the patient's femoral condyle), and to indicate this deviation to the surgeon.

Furthermore, upon completion of a femoral cut and as the surgeon prepares to place a real tibial cutoff guide on a patient's right tibia in the foregoing example, the computer system can similarly generate an AR frame that—when displayed by the AR device—shows a virtual tibial cutoff guide snapped to the patient's right tibia in the surgeon's field of view. The computer system can then implement methods and techniques as described above to augment the surgeon's field of view with guidance for placement of the real tibial cutoff guide on the patient's right tibia. The computer system can therefore augment the surgeon's field of view with virtual surgical content based on the current state or stage of the surgery.

In one example of a variation of the first method S100, the real surgical guide can be electrically coupled to the computer system, such that when the surgical guide is placed within the threshold offset from the real target location of the surgical guide, the surgical guide (itself) provides feedback—such as haptic vibration or—to the surgeon indicating a correct placement of the surgical guide in the surgical field.

The computer system can implement similar methods and techniques to locate a virtual artificial component—such as a virtual artificial femoral component of a complete artificial knee system or of a femoral head component of an artificial hip implant—within the virtual surgical environment and to generate an AR frame showing the virtual artificial component aligned with a tissue of interest in a surgeon's field of view in order to guide the surgeon in placing a real artificial component in a patient. For example, the computer system can generate a virtual outline of the femoral head implant identifying the target real location for the femoral head implant in the surgical field and publish the virtual outline of the femoral head implant with the frame to the display overlaid on the image of the patient.

In another example implementation of the first method S100, the computer system can capture the image of the surgical field with a camera attached to a virtual reality headset from a first real viewing location; define a view of the surgical field from a particular viewing location in the surgical field to a focal point in the surgical field; define a virtual perspective of the custom virtual anatomical model from a virtual location corresponding to the particular viewing location in the surgical field directed toward a virtual focal point corresponding to the focal point in the surgical field; generating the frame depicting a projection of the target real location of the surgical guide and/or the target real cut trajectory based on a projection of the virtual location of the virtual surgical guide and the virtual cut trajectory from the virtual perspective; and rendering the frame depicting the projection on a display. In this example, the perspective of the frame rendered on the display can be defined from a location of a camera—offset from the display—toward the surgical field. Alternatively, the perspective of the frame can be defined from a location of the display—offset from the camera—to the surgical field. Thus, in order to render a frame in the display perspective, the computer system can transform (or project) the camera perspective of the surgical field onto the display perspective. Additionally, a surgeon may wish to view the surgical field from a different viewing perspective. The computer system can transform (or project) the camera perspective of the surgical field into any other perspective specified by the computer system and/or an operator of the computer system.

1.6 Virtual Cut Trajectory

One variation of the first method S100 includes Block S162, which recites virtually locating a virtual cut plane to the tissue of interest within a virtual surgical environment; and generating an augmented reality frame representing the virtual cut trajectory within the virtual surgical environment based on a position of an augmented reality headset relative to the tissue of interest in the surgical field in Block S150, as shown in FIG. 1. Generally, in this variation, the computer system can implement methods and techniques similar to those of Block S140 to locate a virtual cut trajectory, virtual cut plane, or cut axis, etc. within the virtual surgical environment in Block S162 and generate an AR frame representing the virtual cut trajectory and the target location of the surgical guide in Block S150.

In the example above in which the surgeon prepares to cut the patient's right femoral condyle in preparation to receive an artificial femoral component, the computer system can generate an AR frame that includes a virtual cut plane aligned to the patient's exposed femoral condyle. Thus, in addition to placing a real femoral cutoff guide on the patient, the surgeon can align a surgical cutting tool (e.g., an orbital bone saw) to the virtual cut plane shown in her augmented field of view and cut the patient's femoral condyle by maintaining alignment between the virtual cutoff plane and a real blade in the surgical cutting tool in her augmented field of view. In this example, the computer system can implement methods and techniques as described above to identify the surgical cutting tool in the surgical field and to generate AR frames including colored overlays (e.g., red and green overlays) in alignment with the surgical cutting tool in the surgeon's field of view based on whether the surgical cutting tool (or a blade or other cutting surface of the surgical cutting tool) is within a preset tolerance of a target cut trajectory defined in the virtual surgical environment according to the surgical plan.

The computer system can implement similar methods and techniques to locate a virtual cut axis, such as for a surgical drill, within the virtual surgical environment and to generate an AR frame showing the virtual cut axis. Similarly, the computer system can locate a virtual fastening axis, such as for a surgical anchor, within the virtual surgical environment and generate an AR frame showing the virtual fastening axis aligned with a tissue of interest in a surgeon's field of view in order to guide the surgeon in placing a surgical fastener in a patient.

One variation of the first method S100 includes: a virtual model of a surgical tool including a cutting surface in Block S114; virtually locating the virtual tool model to the tissue of interest and the virtual surgical guide within a virtual surgical environment in Block S184; generating a first frame representing a first target real location of the virtual tool model within the virtual surgical environment based on a current position of an augmented reality headset relative to the tissue of interest in the surgical field in Block S150; and tracking a position of the real surgical tool within the surgical field environment in Block S170, as shown in FIG. 2. Generally, in this variation, the computer system can implement methods and techniques described above to locate a cutting tool trajectory—defined in the surgical plan—in the virtual surgical environment, to generate a sequence of AR frames showing a virtual surgical tool at various positions along the cutting tool trajectory based on real positions of a corresponding surgical tool detected and identified in the surgical field, and to serve these AR frames to a surgeon during a surgery in order to guide the surgeon in placing and manipulating the surgical tool according to the surgical plan. In this variation of the first method S100, the virtual tool model can include parameters such as a particular cutting surface, a particular surface finish resulting from use of the tool, a cut width of the tool, a maximum cut depth, etc.

In the example above in which the surgeon prepares to cut the patient's right femoral condyle in preparation to receive an artificial femoral component, the computer system can: retrieve a virtual model of a surgical cutting tool in Block S114; locate the virtual cutting tool model in the virtual surgical environment in Block S184 based on the location of an artificial femoral component, the virtual guide, a cut femoral condyle surface, or a target cutting tool trajectory defined in the surgical plan; generate a first AR frame that includes the virtual surgical cutting tool model aligned with an initial target real location in the target cutting tool trajectory in the surgeon's field of view in Block S150; and then serve this first AR frame to the AR device substantially in real-time in Block S160. In this example, as the surgeon moves a real surgical cutting tool toward the patient's exposed femoral condyle in the surgical field, the computer system can implement methods and techniques described above: to identify the surgical cutting tool in an image retrieved from one or more camera(s) in the operating room; to calculate a difference between real position of the surgical cutting tool and the initial target real location in the target cutting tool trajectory; and to generate a subsequent AR frame highlighting this difference and/or including textual or graphical instructions to rotate or translate the surgical cutting tool toward the initial target real location in the target cutting tool trajectory. The computer system can repeat this process with each subsequent image retrieved in Block S140 until the surgical cutting tool is positioned within the surgical field relative to the patient's exposed femur within an angular and linear tolerance of the initial target real location in the target cutting tool trajectory.

Once the surgical cutting tool is thus positioned within the angular and linear tolerance of the initial target real location in the target cutting tool trajectory, the computer system can generate a subsequent AR frame including a second target real location of the surgical cutting tool in the target cutting tool trajectory, such as offset from the initial target real location by a step distance of 0.10" along the target cutting tool trajectory, as shown in FIG. 2. While the surgical cutting tool is active (e.g., while a blade in the surgical cutting tool is rotating) and manually moved from one location to the next along the target cutting tool trajectory, the computer system can track the position of the surgical cutting tool in the surgical field in Block S170 and repeat the foregoing process to generate a sequence of AR frames that augment the surgeon's field of view with visual guidance indicating a next target real location of the surgical cutting tool in the surgeon's field of view until the target cutting tool trajectory is completed.

Thus, with both AR guidance and guidance from a real femoral cutoff guide arranged on the patient, the surgeon can cut the patient's femoral condyle within a tolerance of the target cut trajectory by maintaining alignment between the real surgical cutting tool, a virtual surgical cutting tool in the surgeon's augmented field of view, and the real surgical guide in the surgical field.

Alternatively, in response to a deviation of the actual real cut trajectory from the target real cut trajectory detected in the surgical field, the computer system can record the deviation and update the model of the virtual cut surface with the real cut trajectory. Thus, the computer system can track deviations from the surgical plan and, in real-time, update the target real location for the surgical guide in the surgical field to ensure consistency of each cut during a surgical operation.

In one variation of the first method S100, the real surgical cutting tool can be electrically coupled to the computer system such that when the surgical cutting tool moves outside of the threshold offset from the real cut trajectory, the surgical cutting tool (itself) provides feedback—such as a haptic vibration distributed through the surgical tool—to the surgeon indicating a deviation of the surgical cutting tool from the real cut trajectory.

However, the computer system can implement any other method or technique to generate an AR image that, when rendered on an AR device, augments a surgeon's field of view with guidance for placing a surgical cutting guide, manipulating a surgical tool, placing a surgical tool, installing an artificial element, and/or installing a surgical fastener, etc.

1.7 Surgical Precision

As shown in FIG. 1, in Block S140 of the first method S100, the computer system can also identify a tissue of interest (i.e., a real human feature such as a hard tissue component like bone) within an image of the surgical model, align (e.g., scale, orient, and translate in six axes) patient scan data and/or a surgical model to the tissue of interest within a virtual surgical environment, and locate a virtual surgical guide within the virtual surgical environment based on a surgical plan. For example, the computer system can transform a generic tissue model (e.g., generic bone, muscle, ligament, and arterial tissue model) into a patient-specific tissue model based on real X-ray, MRI, CAT scan, and/or other patient scan data and can then interface with a surgeon to develop a surgical plan—such as including placement of surgical guides, location of a cut plane, location of a drill axis, or trajectory of a surgical tool within the patient-specific tissue model—for the patient's upcoming surgery. The computer system can then locate a surgical guide, a surgical jig, a surgical cut plane, and/or a surgical drill axis, etc. within the patient-specific tissue model. Later, during the surgery, the computer system can align the patient-specific tissue model—with the virtual surgical guide—to a tissue of interest identified in an image of the surgical field, generate an AR frame by projecting the aligned patient-specific tissue model and virtual surgical guide onto the surgeon's field of view, and then serve the AR frame to the surgeon to guide the surgeon in placing the surgical guide and operating a cutting tool within the surgical field. (The computer system can similarly serve an AR frame including a cut plane, a drill axis, or a trajectory of a surgical tool, etc.)

Therefore, by aligning a predefined surgical plan to a tissue of interest within a surgical field and serving AR frames containing virtual surgical guides to the surgeon substantially in real-time, the computer system guides placement of surgical guides, tools, installation of implants, etc. in direct accordance with the predefined surgical plan substantially without necessitating additional inter-operative measurement by the surgeon. For example, the computer system can serve AR frames to a surgeon substantially in real-time during a surgery to reduce positional errors in placement of a tool, an implanted device or mechanism, or implanted tissue, etc. due to redundancy between the AR guidance through virtual frames and precise location of a real surgical guide within the surgical field. By reducing position errors in placement of surgical tools and guides, the first method S100 can thereby extend functional life of an implant and limit a patient's pain from joint misalignment.

Additionally, in one variation of the first method S100, the computer system can track movement of the tissue of interest and, in real-time, realign the custom virtual anatomical model to the tissue of interest in the surgical field in any position.

Figure 7:
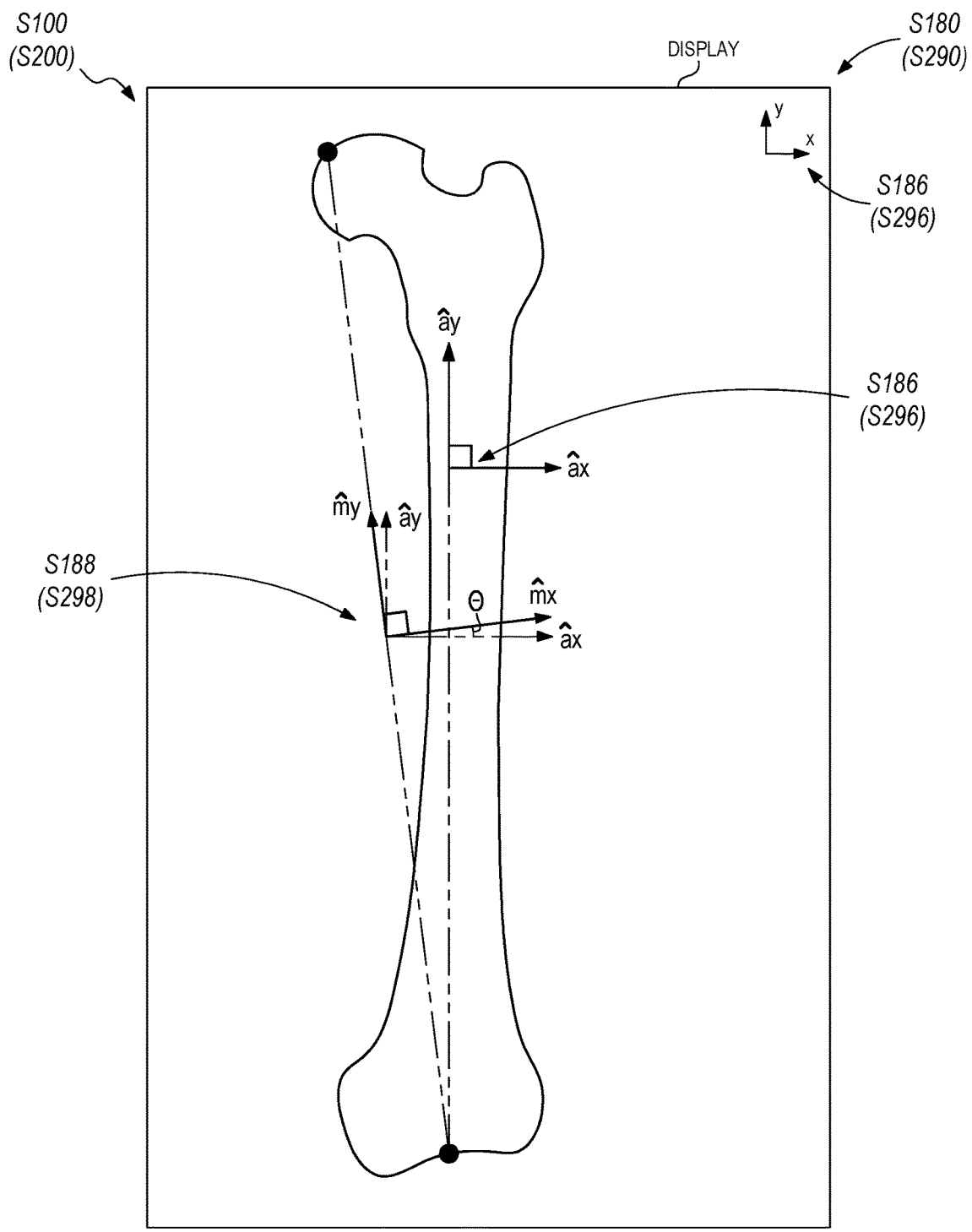
FIG. 7 is a schematic representation of the first method.
Figure 8:
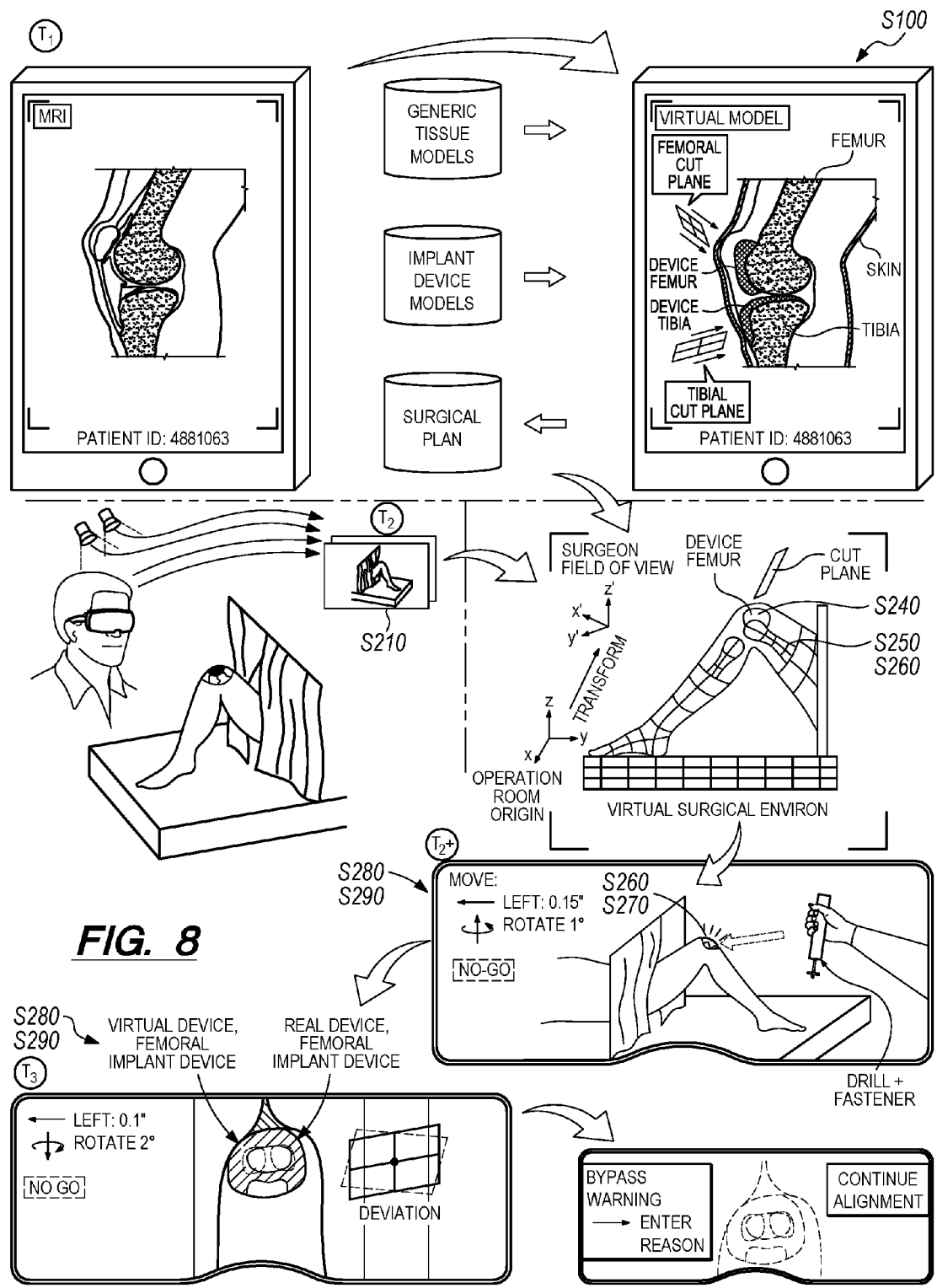
FIG. 8 is a flowchart representation of one variation of the second method.

In one variation of the first method S100 shown in FIG. 7, the computer system can render a coordinate system overlaid on an image of the tissue of interest in the guide frame in Block S186. The computer system can render the coordinates and/or axes indicating an orientation of tissue of interest in Block S188.

1.8 Timing

The computer system can execute Blocks S105 through S130 of the first method S100 sequentially prior to a surgical operation and Blocks S140 through S180 can be implemented substantially in real-time during the surgical operation. Thus, generally, Blocks S105 through S130 can function to pre-plan a surgical operation while Blocks S140 through S180 function to provide real-time feedback to a surgeon during a surgical operation. Alternatively, the computer system can also capture an image of the surgical field at a first time and, at a second time chronologically offset from the first time, serve the guide frame overlaid on the image of the surgical field captured at the first time. In another implementation, the computer system can also execute Blocks of the first method S100 substantially in real-time.

2. Second Method

As shown in FIGS. 5, 6A, 6B, and 8, a second method S200 for augmenting a surgical field with virtual guidance content includes, during the surgical operation on a tissue of interest of a patient: at a first time, accessing an image of a surgical field captured by a sensor coupled to a computing device in the surgical field in Block S210; detecting the tissue of interest in the image in Block S220; accessing a virtual model of a surgical implant corresponding to the tissue of interest in Block S230; aligning a generic virtual anatomical model with the tissue of interest in the image to define a custom virtual anatomical model in Block S240; locating the virtual model of the surgical implant within the custom virtual anatomical model in Block S250; defining a virtual cut trajectory along a boundary of an intersection between the virtual model of the surgical implant and the custom virtual anatomical model of the tissue of interest in Block S260; defining a target real cut trajectory of a surgical tool in the surgical field based on the virtual cut trajectory in Block S270; generating a frame depicting the target real cut trajectory in Block S280; and, at approximately the first time, publishing, to a display, the frame depicting the target real cut trajectory in Block S290.

2.1 Applications

Generally, a computer system can execute Blocks of the second method S200 to generate a sequence of augmented reality ("AR") frames containing a virtual surgical guide and depicting a surgeon's field of view—a surgical field— through an AR headset, AR glasses, another AR device, and/or a display remote from the surgical field. The virtual surgical guide can be oriented from a perspective of the surgeon viewing a real human feature—a tissue of interest— within a surgical field environment. The computer system can present these AR frames to the surgeon through an AR device substantially in real-time, thereby guiding the surgeon's application of real tools within the surgical environment with virtual AR objects while limiting aid of real surgical guides, jigs, and fixtures within the surgical field. Thus, AR guides and objects can virtually guide real-space surgical tools in a real surgery while omitting real surgical guides from the surgical field. Consequently, the second method S200 can function to reduce a number of components introduced into a surgical field while improving precision and consistency of a particular surgical operation. Furthermore, the computer system can execute Blocks of the second method S200 to plan and precisely execute a surgical operation in real-time.

The second method S200 can therefore be implemented in conjunction with an AR device and one or more sensors within a surgical field to replace one or more real jigs, fixtures, or surgical guides. For example, by replacing real surgical guides with virtual surgical guides, the second method S200 can: reduce requirements for real surgical guides to locate real surgical tools during a surgery; reduce a cost to outfit a surgical field with such real surgical guides; reduce a number of real elements introduced into a sterile field during a surgical operation; and/or enable rapid and comprehensive modernization of surgical guides within a surgical setting by updating virtual surgical guides rather than by replacing obsolete real surgical guides with new real surgical guides.

In particular, a computer system can implement Blocks of the second method S200: to identify a tissue of interest within an image of a real surgical field; to align a generic virtual anatomical model to the tissue of interest within a virtual surgical environment to define a custom virtual anatomical model; to determine contents and orientation of components within a surgical field in a surgeon's current field of view; to define a virtual cut in the custom virtual anatomical model; to form an AR frame by projecting the custom virtual anatomical model, the virtual cut trajectory, and the virtual surgical environment onto the surgeon's current field of view; to serve the AR frame to an AR device worn by the surgeon substantially in real-time in order to guide the surgeon's placement and use of a surgical tool within the surgical field; and to repeat this process throughout a surgery to serve updated AR frames to the surgeon substantially in real-time as the surgeon moves relative to the surgical field and to the tissue of interest of the patient and as the surgeon completes various stages of the surgery.

Figure 9:
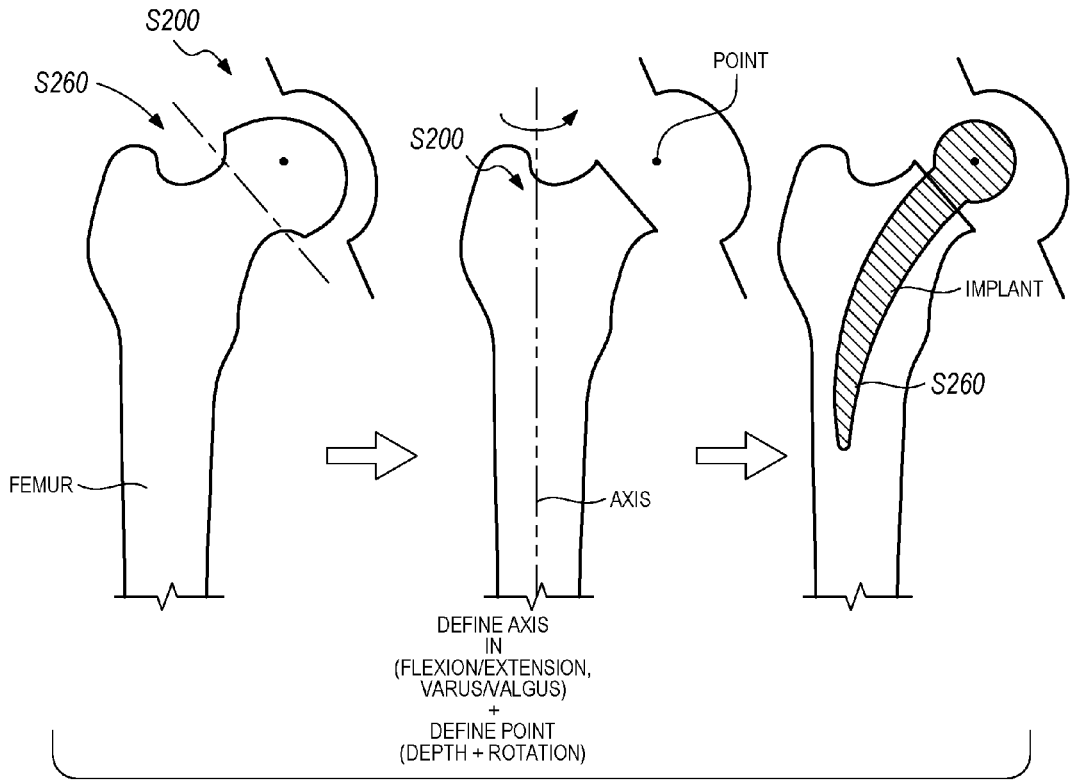
FIG. 9 is a flowchart representation of the second method.
Figure 10:
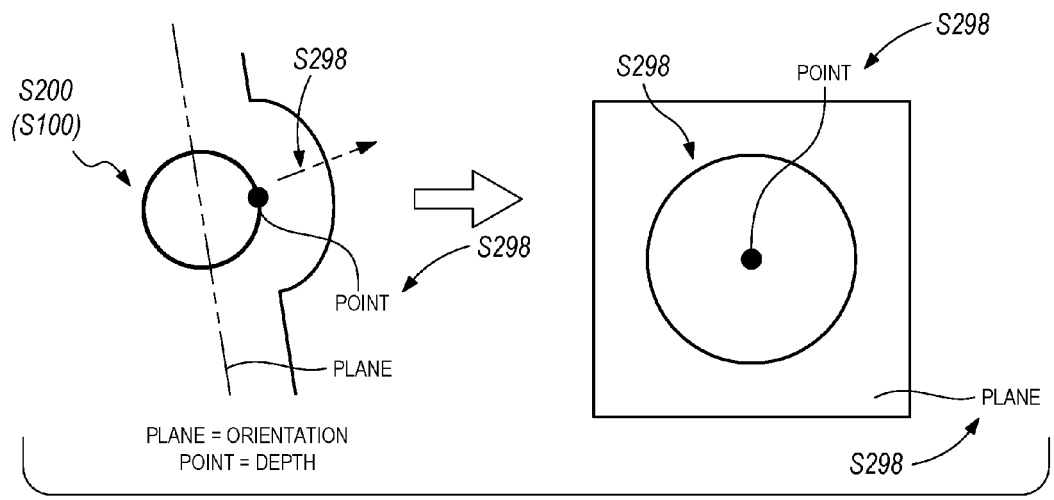
FIG. 10 is a schematic representation of the second method.

In one example application, the computer system can detect a patient recumbent in the surgical field through an augmented reality (AR) headset with an integrated camera (or radar, sonar, or other sensor with which to capture the surgical field). From the image of the surgical field, the computer system can generate a custom (patient-specific) virtual anatomical model. During a hip replacement surgery on the patient (or before the hip replacement surgery as described in method S100), the surgeon and/or the computer system can locate (i.e., arrange or place) a virtual model of a hip implant (a femoral head implant) within the custom virtual anatomical model. From the placement of the virtual model of the hip implant, the surgeon and/or the computer system can define virtual cut trajectories for the hip replacement surgery. As shown in FIGS. 3A, 3B, and 9, the virtual cut trajectories can include a saw cut plane and a reamer cut path. In this example, the saw cut plane can traverse the femoral head and represent a target plane through which a bone saw is to pass through the femoral head, as depicted in FIG. 10. The reamer cut path can define: a cut axis aligned to a mechanical axis of the femur and represented by target line along which the reamer is to pass to ream the femoral neck; and a cut depth aligned to a target stop (e.g., depth) represented by a point at which the reamer is to stop in the femoral neck, as shown in FIGS. 9 and 10. In this example application, the cut depth can be defined by (and aligned with) an acetabular plane of the patient's hip. (The acetabular plane can be defined by anteversion and inclination angles of the opening of acetabulum. Orientation of the acetabular plane can be detected in the image of the surgical field by the computer system or can be defined by the computer system pre-operatively based on pre-operative scans of the patient).

The computer system can then generate a frame depicting a 3D representation of the cut plane and the reamer cut path, such as by aligning the saw cut plane and the line and the point of the reamer cut path (i.e., "virtual guides") to the tissue of interest detected in an image of the surgical field and then projecting the saw cut plane and reamer cut path onto a field of view of a display (e.g., an AR eyes-up display or a monitor) in the surgical field. The computer system can also incorporate a virtual representation of positional coordinate axes of the femur, such as relative the acetabulum, in the frame. Thus, in this example application, the computer system can generate a frame containing virtual visual guides for placement of surgical tools (e.g., a bone saw and a reamer) within the surgical field relative to the patient; the surgeon can then manipulate these surgical tools within the surgical field based on these virtual visual guides.

A computer system executing Blocks of the second method S200 can automatically register a patient's bone or other tissue to a reference within the operating room or within the surgical field in real-time during a surgery based on non-contact data collected during the surgery and without necessitating introduction of additional reference features into the surgical field, such as an infrared light array or reflective element that must be fastened to a patient's bone. In particular, by registering a region of a patient's body directly in a feed of depth and/or color images rather than detecting an additional reference mounted or fixed to the patient, the computer system executing the second method S200 can enable a surgeon to focus on operations directly related to the surgery at hand and avoid additional steps to manually register or to guide a computer in registering a bone or other tissue feature of the patient. Furthermore, by registering the patient's tissue directly rather than an additional reference feature mounted or fixed to the patient's body, fewer components may be introduced to the surgical field during the surgery, which may reduce vectors for infection, post-operative patient pain (e.g., from drilling into a bone to mount an infrared light array with a mechanical fastener), and other complications related to surgery.

Blocks of the second method S200 can be executed locally and/or remotely, such as by a local computer system within an operating room or within a hospital, by a remote computer system (e.g., a remote server), and/or by a distributed computer network, etc. Blocks of the second method S200 can additionally or alternatively be executed by an AR headset, AR glasses, or other AR device. A device executing Blocks of the second method S200 can also interface with: an AR device; one or more cameras and distance (e.g., LIDAR) sensors; sensor-enabled tools; and/or other sensors and actuators within the operating room. However, any other one or more local, remote, or distributed computer systems can execute Blocks of the second method S200 substantially in real-time.

Blocks of the second method S200 are described herein in the context of a knee replacement and a hip replacement. However, Blocks of the second method S200 can be executed by a computer system to generate and serve AR frames depicting virtual cut trajectories for any other surgical application, such as: a hip replacement operation; a heart valve replacement operation; a carpel tunnel release surgery; a cataract removal procedure; a cholecystectomy procedure; etc. Furthermore, Blocks of the second method S200 are described herein in the context of serving virtual guidance for placement and operation of surgical cutting tools during a surgery. However, Blocks of the second method S200 can be executed by a computer system to serve virtual guidance for placement of a fastener (e.g., a surgical anchor, a fusion plate), placement of an implant (e.g., a metal head, an acetabular component, a plastic liner for a hip replacement), or placement of any other tool or object within a surgical field in real-time. Blocks of the second method S200 can be executed by a computer system tracking a region of a patient's body, to identify differences between an operation of the region of the patient's body and a pre-defined surgical plan, and to serve a form of these differences to a surgeon in (near-) real-time during a surgery or operation of any type. Furthermore, Blocks of the second method S200 are described herein in the context of serving virtual guidance for deviations between target and actual location of a cut and target and actual positions of an implant device. However, Blocks of the second method S200 can be executed by a computer system to serve virtual guidance for differences between target and actual location of a fastener, a cutting tool, a portion of an implant device (e.g., a tibial canal insert extending from an artificial tibial component), or any other tool or object within a surgical field.

2.2 Image of the Surgical Field

Block S210 of the first method S100 recites, during the surgical operation on a tissue of interest of a patient: at a first time, accessing an image of a surgical field captured by a sensor (i.e., an optical sensor) coupled to a computing device in the surgical field. Generally, in Block S210, the computer system interfaces within one or more cameras or other sensors to collect images of a surgical field.

In one implementation, the computer system collects images from sensors arranged at static, known locations within the operating room. For example, pairs of depth sensors and color cameras can be arranged in two or more corners of the operating room and directed toward an operating table at the center of the operating room. In another example, a depth sensor and a color camera can be arranged directly over and pointing downward at the operating table. The computer system can thus collect a feed of depth images and a feed of color images from the depth sensor and color camera pairs, and the computer system can implement edge detection, object recognition, and/or other machine vision techniques to detect features within these images and to define a coordinate system relative to the operating room or to an operating table accordingly.

The computer system can additionally or alternatively collect image feeds from sensors mounted on a human or on a mobile platform arranged within the operating room. For example, the computer system can download digital photographic color images from a forward-facing camera arranged on each side of an AR headset worn by a surgeon during the surgery. In these examples, the computer system (or a remote computer contracted by the computer system) can stitch images captured substantially simultaneously by two or more cameras within the operating room into a 3D point cloud or other 3D image of a volume within the operating room (hereinafter "3D surgical field image"). The computer system can also collect feeds of depth and/or color images simultaneously from AR headsets worn by multiple surgeons and/or nurses within the operating room during the surgery.

Furthermore, the computer system can interface with sensors arranged both statically within the operating room and dynamically within the operating room, such as mounted to humans or to mobile platforms within the operating room. For example, during a surgery, a surgeon and a nurse can each wear an AR headset including an integrated depth sensor, one or more color cameras, and a set of active or passive optical fiducials (e.g., IR emitters or reflective surfaces). In this example, one or more depth sensors and/or color cameras can also be arranged statically within the operating room. Upon receipt of a set of depth and/or color images from the static sensor(s), the computer system can detect fiducials on the AR helmets in these images and calculate the location of each AR headset within the operating room at the corresponding time relative to a known reference point or coordinate system previously defined for the operating room. Upon receipt of a set of depth and/or color images from sensors on one of the AR headsets at a particular time, the computer system can: stitch a set of depth and color images into a 3D point cloud or into a 3D color image relative to the AR headset; merge these 3D images with 3D images generated from data received from the other AR headset at a similar time into a 3D surgical field image—containing a greater density of data and fewer blind spots due to multiple fields of view from which the 3D surgical field image originated—based on known locations of the AR headsets relative to the operating room coordinate system at the particular time; and then transform the 3D surgical field image onto the coordinate system of the operating room in (near-) real-time (As shown in FIG. 7, the computer system can render the coordinate system, overlaid on an image of the tissue of interest in the guide frame in Block S296. The computer system can render the coordinates and/or axes indicating an orientation of the guide frame in Block S298). The computer system can repeat this process for each set of depth and/or color images received from the static sensors and from the AR headsets to generate one 3D surgical field image per scan period or set of scan periods performed by the sensors during a surgery.

The computer system can thus fuse data collected from sensors arranged statically and dynamically within the operating room to generate 3D surgical field images exhibiting high spatial accuracy, exhibiting minimal voids, and containing data representing a specific and relatively narrow area of interest within the operating room (e.g., a particular region of the patient's body undergoing surgery and consistently viewed by a nurse or surgeon). In particular, by combining images received from multiple AR headset-mounted sensors into a composite image based on positions of the AR headsets determined from depth images output by sensors arranged statically in the operating room, the computer system can maintain a relatively high ratio of interest area to processed image area for each 3D surgical field image and faster and/or less expensive generation and analysis of these 3D surgical field images.

The computer system can collect one or more depth and/or color images in Block S220 and process these images as described below substantially in real-time. The computer system can collect images from one or more cameras or distance data from one or more other sensors at a frame rate similar to a projection frame rate of the AR headset (or other AR device) worn by the surgeon during the surgery, such as thirty frames per second. However, the computer system can collect any other color, distance, or other data from any other type of sensor arranged in any other way within an operating room.

2.3 Tissue Detection

Block S220 of the first method S100 recites detecting the tissue of interest in the image; and Block S240 recites aligning a generic virtual anatomical model with the tissue of interest in the image to define a custom virtual anatomical model. In one implementation, the computer system can process the 3D surgical field image to identify a human feature in the real surgical field in Block S220 and can then align a generic virtual anatomical model to the human feature within the virtual surgical environment in Block S240. By mapping an image of a surgical field to the generic anatomical model the computer system can thus locate a virtual cut trajectory and other useful surgical guidance metrics within a virtual surgical environment. By thus mapping a generic virtual tissue model within the virtual surgical environment onto real patient tissue identified in the 3D surgical field image in Block S240, the computer system can later generate an AR frame containing virtual content aligned to real patient tissue in the surgical field in Block S280 and S290 by projecting the virtual surgical environment onto the surgeon's known or calculated field of view, as described below.

In one example in which a patient's right knee is undergoing a total knee replacement, the computer system can: identify the patient's right leg in the 3D surgical field image in Block S220; and map generic virtual knee model onto the patient's right leg in the 3D surgical field image to define (e.g., orient) a patient-specific virtual knee model in the virtual surgical environment in Block S240. In this example, the computer system can implement object detection, edge detection, surface detection, and/or any other computer vision technique to distinguish distinct volumes or surfaces in the 3D surgical field image; the computer system can then compare a generic virtual tibia model—within a generic virtual knee model of a greater right leg—to these distinct volumes or surfaces in the 3D surgical field image to identify the patient's lower right leg represented in the 3D surgical field image. Similarly, the computer system can compare a generic virtual femur model—within the generic virtual tissue model of the greater right leg—to these distinct volumes or surfaces in the 3D surgical field image to identify the patient's right thigh represented in the 3D surgical field image. By separately scaling, rotating, and translating the patient-specific virtual tibia model and the patient-specific virtual femur model into alignment with like volumes or surfaces in the 3D surgical field image, the computer system can locate and align each side of a virtual articulable knee joint model in the virtual surgical environment to the real position of the patient's right leg in the surgical field in Block S240.

In the foregoing implementation, the computer system can compare various tissue types in the virtual patient-specific tissue model and in the 3D surgical field image to align the virtual patient-specific tissue model to the 3D surgical field image in Block S240. In particular, the computer system can implement edge detection, color matching, texture recognition, and/or other computer vision techniques to distinguish skin, muscle, bone, and other tissue in the surgical field image. The computer system can then identify points or surfaces in the surgical field image accordingly and scale, translate, rotate, and/or otherwise manipulate virtual surfaces or virtual volumes in the patient-specific knee model into alignment with corresponding labeled surfaces in the patient-specific knee model. The computer system can therefore detect different types of tissue within the surgical field and dynamically map a virtual patient-specific tissue model to one or more tissue types throughout a surgery as the patient's body is manipulated and as different tissues are exposed.

The computer system can implement template matching techniques to match template tissue point clouds—labeled with one or more anatomical tissue labels—to tissue masses identified in the 3D point cloud and transfer anatomical tissue labels from matched template tissue point clouds to corresponding tissue masses in the 3D point cloud. Yet alternatively, the computer system can: implement computer vision techniques, such as edge detection or object recognition, to automatically detect distinct tissue masses in the scan data and write an anatomical tissue label to each distinct tissue mass in the 3D point cloud based on anatomical tissue labels manually entered or selected by the surgeon through the surgeon portal. However, the computer system can implement any other method or technique to label tissues within a surgical field image automatically or with guidance from a surgeon.

Figure 5:
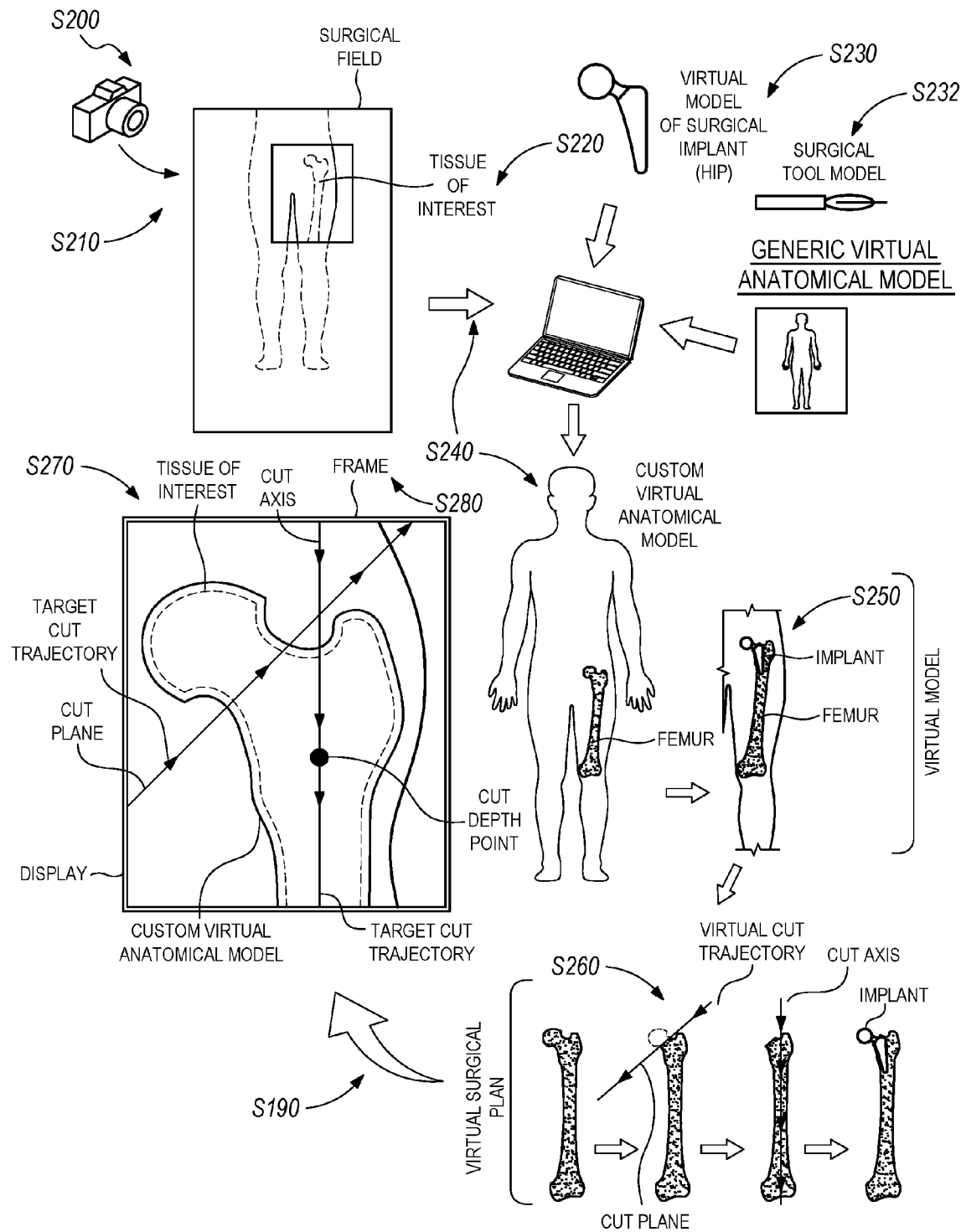
FIG. 5 is a flowchart representation of a second method.

In another implementation, the computer system can scale, articulate, translate, rotate, or otherwise manipulate virtual tissue objects within a generic virtual anatomical model of a similar region of a human body into alignment with corresponding labeled tissue masses in the 3D point cloud, as shown in FIG. 5. For example, the computer system can: locally scale and reorient surfaces of a generic virtual tibia to mimic the geometry of a tibia labeled in the 3D point cloud; locally scale and reorient surfaces of a generic virtual quadriceps muscle to mimic the geometry of a quadriceps muscle labeled in the 3D point cloud; locally scale and reorient surfaces of a generic virtual iliotibial band to mimic the geometry of an iliotibial band labeled in the 3D point cloud; and locally scale and reorient generic virtual skin—around the virtual customized tibia, the virtual customized quadriceps muscle, and the virtual customized iliotibial band—to mimic the geometry of the exterior of the patient's leg shown in the 3D point cloud. The computer system can thus generate a patient-specific virtual tissue model of a region of the patient's body scheduled for surgery by merging real patient scan data with a generic virtual anatomical model of a human body or region of a human body.

Additionally, in one variation of the second method S200, the computer system can track movement of the tissue of interest and, in real-time, realign the custom virtual anatomical model to the tissue of interest in the surgical field in any position. For example, in a hip replacement surgery, the tissue of interest—the femur—may shift positions during the surgical operation, either intentionally or inadvertently. The computer system can implement Blocks of the second method S200, to access: an image, at a first time, of the surgical field and detect the femur in a first position; and an image, at a second time, of the surgical field and detect the femur in a second position distinct from the first position. By tracking movement of the femur, the computer system can, in real-time, consistently update the (virtual) guide frame rendered in a display (such as in a display of a virtual reality head set) to depict the real target cut trajectory in the surgical field for the femur in any position or orientation in the surgical field. Thus, the computer system can improve cut precision during an operation by updating the guide frame to correspond with the position, location, and rotation of the tissue of interest in real-time.

In the preceding example of a hip replacement surgery, at a first time, the tissue of interest—the femur—can be arranged in a first position in the surgical field. In this example, a planned cut trajectory for insertion of a femoral head implant can be aligned with a mechanical axis of the femur. By accessing the custom virtual anatomical model of the femur, the computer system can determine an anatomical axis of the femur (i.e., a central axis through the center of a femoral shaft). The computer system can also define the mechanical axis from a center of a femoral head of the femur to a medial tibial spine in the custom virtual anatomical model and/or from scan data accessed by the computer system. The computer system can then generate a new guide frame to include an image of the mechanical axis overlaid on the femur. Alternatively, the computer system can implement Blocks of the second method S200 to, at a first time, access an image of the surgical field and detect the femur in a first position; and, at a second time, access an image of the surgical field and detect the femur in a second position distinct from the first position. By tracking movement of the femur from a first position, the computer system can isolate a pivot point (or origin) about which the femur moves and, from the pivot point, extract the mechanical axis of the femur.

Alternatively, the computer system can align patient scan data (rather than the patient-specific tissue model) to a tissue of interest identified in the 3D surgical field image and can locate 3D patient scan data within the virtual surgical environment according to the position of the tissue of interest in the surgical field.

2.4 Registration Hierarchy

In one implementation of the second method S200, the computer system implements a registration hierarchy to detect features within the operating room and to register a particular region of a patient's body for precise location of a virtual tissue model from a surgical plan to real space as additional image data becomes available throughout a surgery. In this implementation, the computer system can first register the operating room (e.g., by defining a coordinate system for the operating room) from a first sequence of images received from sensors mounted statically within the operating room, such as before the surgery commences. Once the operating room is registered, the computer system can implement pattern matching, object recognition, and/or other computer vision techniques to identify an operating table (or fiducials installed on the operating table) within the operating room from the same set or from a subsequent set of images received from the static sensors. The computer system can then process images from the static sensors or from sensors arranged on an AR headset worn by a surgeon—and registered relative to the operation room coordinate system, as described above—to identify a patient on the operating table. For example, the computer system can implement facial recognition or pattern matching techniques to identity the patient's body or particular features of the patient's body in images received from sensors within the operating room. In another example, the computer system can detect fiducials placed on the patient's skin prior to surgery—such as reference stickers placed on the patient's forehead, abdomen, shoulders, and thighs—within such images to locate the patient relative to the operating room coordinate system.

In the foregoing implementation, once the patient's body is identified in an image and registered within the operating room, the computer system can identify a particular limb, joint, or region of the patient's body designated for surgery. For example, the computer system can: implement edge detection techniques to detect a perimeter of the patient's body within a 3D surgical field image; and then bound a region within this perimeter of the patient's body in which a limb, joint, or other tissue designated for the surgery is likely to be located, such as a first quadrant of this region of the 3D surgical field image for the patient's left arm and a third quadrant of this region of the 3D surgical field image for the patient's right knee. The computer system can thus implement computer vision techniques and known locations of limbs, joints, or other tissues relative to a human body generally to detect and register a particular region of a 3D surgical field image corresponding to a region of the patient's body designated for a surgical operation.

In one variation, a surgeon or nurse manipulates a limb according to a motion procedure prior to beginning the operation (e.g., prior to a first cut), and the computer system detects and tracks movement of the limb and registers the limb within the operating room according to detection of movement of the limb. In one example, for a patient about to undergo a full replacement surgery of his right knee, a surgeon may manipulate the patient's right knee between full flexion and full extension at each of a full medial position, a neutral position, a full lateral position, a full abduction position, and a full adduction position of the hip according to a pre-described motion procedure. In this example, the surgeon can also hold the patient's right leg straight while rotating the hip from a full medial rotation to a full lateral rotation, then from a full flexion position to a maximum extension position possible given the operating table below, and then from a full adduction position to a full abduction position according to the pre-described motion procedure. The surgeon can similarly manipulate the patient's ankle. In this variation, once a relevant region of the patient's body is identified and bounded within one 3D surgical field image, as described above, the computer system can implement object tracking techniques to track this relevant region of the patient's body within a subsequent stream of 3D surgical field images. Thus, as the surgeon manipulates the patient's right leg, the computer system can track movement of the leg through various ranges of motion.

In this variation, the computer system can then interpolate articulation axes of one or more joints within or connected to the manipulated limb based on trajectories of the manipulated limb across a sequence of 3D surgical field images, and the computer system can represent each articulation axis in a virtual model of the patient within the virtual surgical environment. The computer system can further connect articulation axes in the virtual patient limb model with a virtual line or with a virtual tissue model to further develop a virtual model of the patient within the virtual surgical environment. Similarly, the computer system can scale a generic virtual bone model—of the correct bone type for the patient's imaged limb—to fit between the two articulation axes in the virtual patient limb model in order to generate a customized, patient-specific bone model in real-time during the operation. The computer system can further match these empirical articulation axes to known articulation axes and common articulation ranges of joints, such as defined in a human skeletal model, to confirm identification of the limb tracked across 3D surgical field images.

Once a limb or other region of the patient's body designated for surgery is identified in a 3D surgical field image, the computer system can align a virtual bone model to features detected on the uncut limb or other region of the patient's body. For example, the computer system can: detect a medial ridge along the patient's lower right leg in the 3D point cloud; adjust the pitch, yaw, roll, and lateral and longitudinal positions of a virtual tibia model within the virtual surgical environment to align the anteromedial surface of the virtual tibia model to the medial ridge shown in a 3D surgical field image. The computer system can additionally or alternatively calculate a confidence score for the determined position of the patient's bone within the surgical field based on a magnitude of deviations between the position of a virtual bone model placed between articulation axes within the virtual surgical environment and the position of the patient's corresponding bone within the surgical field determined from extracutaneous features on the patient's limb.

Throughout the surgery, as soft tissue is cut and shifted relative to the patient's skeletal structure, the computer system can identify such soft tissue (e.g., muscle, cartilage, blood vessels, blood) around a surgical target in a 3D surgical field image and refine virtual tissue models in the virtual surgical environment based on such soft tissue data. For example, as a cut is made through the patient's skin and then through muscle, the computer system can detect red pixels in the 3D surgical field image, define a volume of interest coincident with these red pixels in the 3D surgical field image, implement object tracking to track soft tissue across a subsequent sequence of 3D surgical field images, and crop these subsequent 3D surgical field images to include substantially only soft tissue within and around a cut. The computer system can then narrow analysis of subsequent 3D surgical field images to only these cropped regions showing this volume of interest in order to reduce processing time of 3D surgical field images without substantially sacrificing accuracy of the patient limb tracking and/or registration of the patient's body within the surgical field.

Once a target tissue specified in the surgical plan is exposed during the surgery, the computer system can identify this target tissue and refine registration of the target tissue within the surgical environment and update virtual tissue models in the virtual surgical environment accordingly. In particular, once bone is exposed and visible within a 3D surgical field image, the computer system can refine the rotational and translational position of a corresponding virtual bone model in the virtual surgical environment to align with the exposed bone in the real surgical field. For example, for a knee replacement, once the lateral and medial condyles of the patient's tibia are exposed following displacement of the patella and surrounding muscle tissue, the computer system can: identify smooth, white bone in the 3D surgical field image; generate a virtual 3D mesh representing the exposed end of the tibia within the 3D surgical field image; and shift the position of a virtual tibia model within the virtual surgical environment to align with the 3D mesh. In this example, the computer system can also modify the geometry of the virtual tibia model to align with the 3D mesh, such as to generate a patient-specific virtual tibia model based on data collected during the surgery substantially in real-time.

The computer system can implement the foregoing methods and techniques over a sequence of 3D surgical field images to refine registration of patient tissue within the surgical field. The computer system can also implement the foregoing methods and techniques over one or more 3D surgical field images to update registration of patient tissue within the surgical field, such as while the patient's limb or torso is moved by a nurse or surgeon during a surgical operation.

However, the computer system can implement any other methods or techniques to identify a patient's tissue within the surgical field, to register (i.e., locate) this tissue within the surgical field relative to a coordinate system, and to refine and update the known location of this tissue throughout the operation. 2.5 Virtual Model The computer system can then access a virtual model of a surgical implant corresponding to the tissue of interest in Block S230; and locate the virtual model of the surgical implant within the custom virtual anatomical model in Block S250. Generally, once the image of the surgical field with the patient is aligned with the generic virtual anatomical model and, thus, transformed into a (patient-specific) custom virtual anatomical tissue model, the computer system can retrieve virtual models of one or more implanted devices, surgical tools, surgical guides, surgical fasteners, etc. and place these within the patient-specific virtual tissue model (or within the 3D point cloud, or within the 3D scan data, etc.) based on a type of surgery selected by the surgeon. In the foregoing example in which the surgery is a total knee replacement, the computer system can retrieve virtual models for an artificial femoral component, an artificial tibial component, and an artificial patellar component (such as based on a knee replacement size selected by the surgeon). In this example, the computer system can then automatically place the artificial femoral, tibial, and patellar components in target implant positions within the patient-specific virtual tissue model based on locations of the original human femur, tibia, and patella within the patient-specific virtual tissue model. The computer system can then serve the patient-specific virtual tissue model with the artificial femoral component, the artificial tibial component, and the artificial patellar component positioned accordingly on the virtual femur and virtual tibia in the patient-specific virtual tissue model to the surgeon through the surgeon portal as shown in FIG. 5.

The computer system can locate the virtual model of the surgical implant within the custom virtual anatomical model by aligning an axis of the surgical implant in the virtual model with a corresponding axis of the tissue of interest in the custom virtual anatomical model; aligning a feature of the surgical implant in the virtual model with a corresponding feature of the tissue of interest in the custom virtual anatomical model; based on the target real cut trajectory, defining a target real location for the surgical implant in the surgical field; and amending the frame to depict a virtual outline of the surgical implant identifying the target real location for the surgical implant in the surgical field.

The virtual model of the surgical implant can also include recommended cutting and alignment information for the surgical implant. For example, the virtual model of Block S230 can be a 3D representation of the surgical implant in which, when integrated with the custom virtual anatomical model of Blocks S230 and S250, the custom virtual anatomical model can reflect a recommended cut surface finish of a recommended surgical tool and a recommended surgical cut contour specified with the virtual model of the surgical implant. The virtual model of the surgical implant can also include recommended cut geometries and depth, ideal alignment, screw and pin dimensions, and other surgical information to generate a realistic model of a human anatomy with an implanted surgical implant.

Block S260 of the second method S200 recites defining a virtual cut trajectory along a boundary of an intersection between the virtual model of the surgical implant and the custom virtual anatomical model of the tissue of interest; Block S270 recites defining a target real cut trajectory of a surgical tool in the surgical field based on the virtual cut trajectory; and Block S280 recites generating a frame depicting the target real cut trajectory. Generally, the computer system can implement methods and techniques to locate a virtual cut trajectory, a virtual cut plane, and/or a virtual cut axis, etc. within the surgical environment and can generate an AR frame representing the virtual cut trajectory in Block S280.

In an example in which the surgeon prepares to cut a patient's right femoral condyle in preparation to receive an artificial femoral component, the computer system can generate an AR frame that includes a virtual cut trajectory—in the form of a virtual cut plane—aligned to the patient's exposed femoral condyle. Thus, the surgeon can align a surgical cutting tool (e.g., an orbital bone saw) to the virtual cut trajectory (a virtual cut plane) shown in the surgeon's augmented field of view and cut the patient's femoral condyle by maintaining alignment between the virtual cutoff trajectory and a real blade in the surgical cutting tool in the surgeon's augmented field of view. In this example, the computer system can implement methods and techniques as described above to identify the surgical cutting tool in the surgical field and to generate AR frames including colored overlays in alignment with the surgical cutting tool in the surgeon's field of view based on whether the surgical cutting tool (or a blade or other cutting surface of the surgical cutting tool) is within a preset tolerance of a target cut trajectory defined in the virtual surgical environment according to the surgical plan.

The computer system can implement similar methods and techniques to locate a virtual cut axis, such as for a surgical drill, or a virtual cut path within the virtual surgical environment and to generate an AR frame showing the virtual cut axis or virtual cut path. Similarly, the computer system can locate a virtual fastening axis, such as for a surgical anchor, within the virtual surgical environment and generate an AR frame showing the virtual fastening axis aligned with a tissue of interest in a surgeon's field of view in order to guide the surgeon in placing a surgical fastener in a patient.

One variation of the second method S200 includes: accessing a virtual model of a surgical tool defining a cut width and a cut surface finish in Block S232; virtually locating the virtual tool model to the tissue of interest within a virtual surgical environment in Block S210; generating a first frame representing a first target real location of the virtual tool model within the virtual surgical environment based on a current position of an augmented reality headset relative to the tissue of interest in the surgical field in Block S280; and tracking a position of the real surgical tool within the surgical field environment in Block S292, as shown in FIG. 2. Generally, in this variation, the computer system can implement methods and techniques described above to locate a cutting tool trajectory in the virtual surgical environment, to generate a sequence of AR frames showing a virtual surgical tool at various positions along the cutting tool trajectory based on real positions of a corresponding surgical tool detected and identified in the surgical field, and to serve these AR frames to a surgeon during a surgery in order to guide the surgeon in placing and manipulating the surgical tool according to the surgical plan.

In this variation, as the surgeon moves a real surgical cutting tool toward the patient's exposed femoral condyle in the surgical field, the computer system can implement methods and techniques described above: to identify the surgical cutting tool in an image retrieved from one or more camera(s) in the operating room; to calculate a difference between real position of the surgical cutting tool and the initial target real location in the target cutting tool trajectory; and to generate a subsequent AR frame highlighting this difference and/or including textual or graphical instructions to rotate or translate the surgical cutting tool toward the initial target real location in the target cutting tool trajectory. The computer system can repeat this process with each subsequent image retrieved in Block S210 until the surgical cutting tool is positioned within the surgical field relative to the patient's exposed femur within an angular and linear tolerance of the initial target real location in the target cutting tool trajectory.

Once the surgical cutting tool is thus positioned within the angular and linear tolerance of the initial target real location in the target cutting tool trajectory, the computer system can generate a subsequent AR frame including a second target real location of the surgical cutting tool in the target cutting tool trajectory, such as offset from the initial target real location by a step distance of 0.10" along the target cutting tool trajectory, as shown in FIG. 2. While the surgical cutting tool is active (e.g., while a blade in the surgical cutting tool is rotating) and manually moved from one location to the next along the target cutting tool trajectory, the computer system can track the position of the surgical cutting tool in the surgical field and repeat the foregoing process to generate a sequence of AR frames that augment the surgeon's field of view with visual guidance indicating a next target real location of the surgical cutting tool in the surgeon's field of view until the target cutting tool trajectory is completed.

Thus, the surgeon can cut the patient's femoral condyle within a tolerance of the surgical plan by maintaining alignment between the real surgical cutting tool and a virtual surgical cutting tool in the surgeon's augmented field of view.

In one implementation, the computing system can identify a particular virtual surgical tool in a set of virtual surgical tools; access a virtual model of the particular virtual surgical tool; identify a shape of the cutting surface of the particular virtual surgical tool and, from the shape of the cutting surface of the particular virtual surgical tool, defining a cut profile of the particular virtual surgical tool; define a cut trajectory with a direction, a depth, and a cut contour defined by a surface of—and specified by—the surgical implant model; and select the particular virtual surgical tool from the set of virtual surgical tools, the cut profile of the particular virtual surgical tool corresponding to the cut contour of the virtual cut trajectory. In general, in this implementation of the variation, the virtual models of the surgical tool and the surgical implant can be used to automatically select an appropriate surgical tool corresponding to a particular cut surface or trajectory defined by the custom virtual anatomical model, the surgical implant (i.e., manufacturer's recommendations for bone surface finish and contour of a bone accepting the surgical implant), and/or known tooling preferences of a particular surgeon.

Figure 6A:
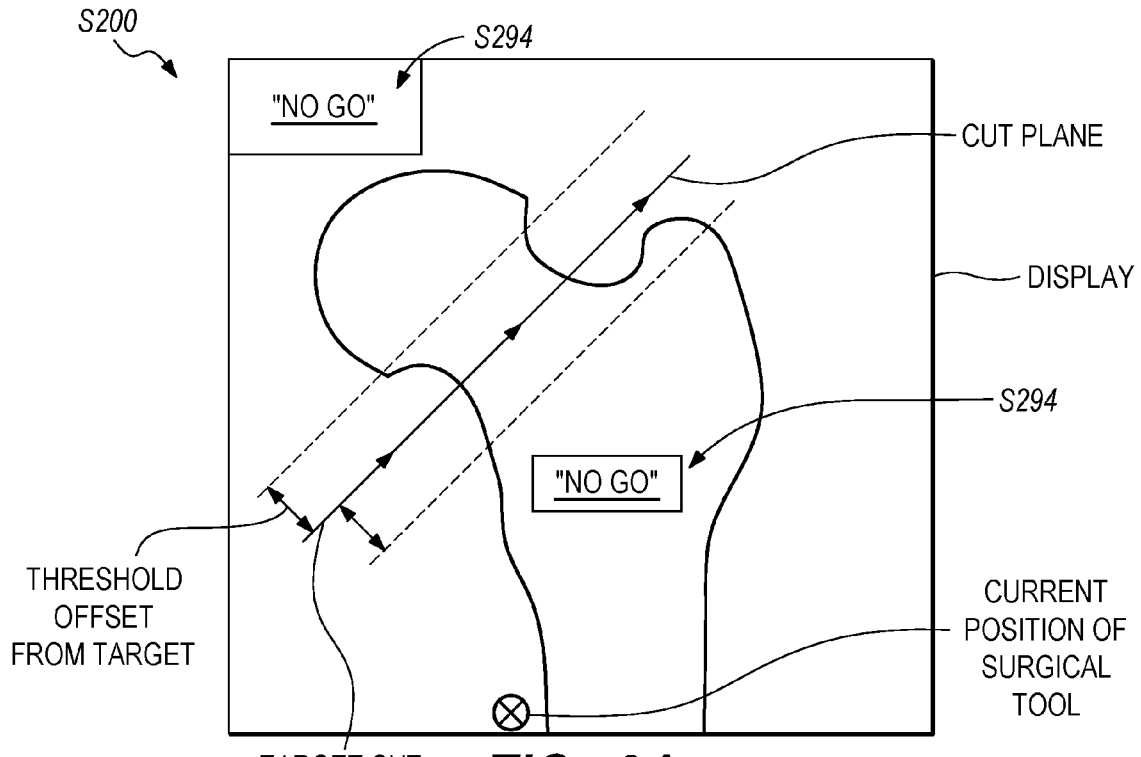
FIGS. 6A and 6B are a flowchart representations of one variation of the second method.
Figure 6B:
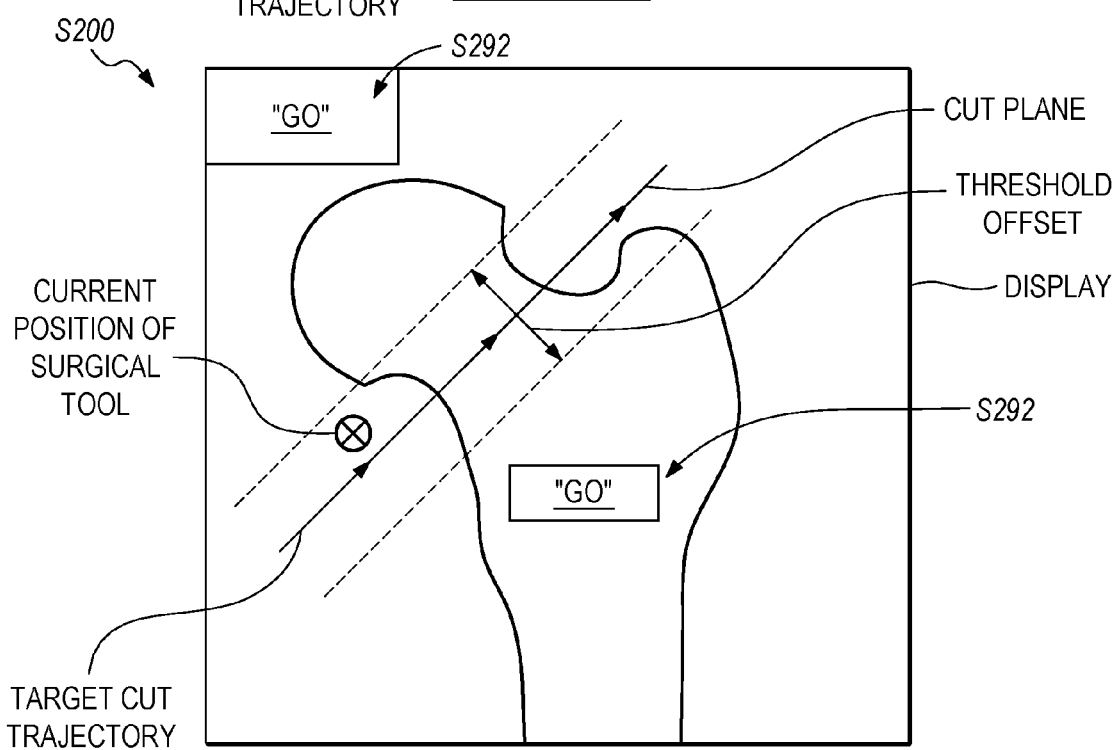

In one implementation of the second method S200 shown in FIGS. 6A and 6B, in response to the real location of the surgical tool within a threshold distance from the target real cut trajectory, the computing system can render a cut approval graphic in the display in Block S292; and, in response to a real location of the surgical tool outside the threshold distance from the target real cut trajectory, rendering a guide frame indicating a direction and a distance of the surgical tool from the target real cut trajectory in Block S294.

However, the computer system can implement any other method or technique to generate an AR image that, when rendered on an AR device, augments a surgeon's field of view with guidance for manipulating a surgical tool, placing a surgical tool, installing an artificial element, and/or installing a surgical fastener, etc.

2.6 Augmented Reality Frame

Block S280 of the second method S200 recites generating a frame depicting the target real cut trajectory; and Block S290 of the second method S200 recites publishing, to a display, the frame depicting the target real cut trajectory. Generally, in Block S280, the computer system transforms locations of the virtual cut plane in a current instance of the virtual surgical environment into a 2D or 3D AR guide frame, indicating target real cut trajectory in the surgical field, based on the surgeon's current field of view or a preferred perspective of the surgical field. The computer system can then serve the AR frame to the surgeon via the AR device in Block S290, thereby supplementing the surgeon's field of view with virtual guides indicating where the surgeon should place a (real) cutting tool.

In one implementation in which the computer system retrieves images recorded by cameras integrated into the AR device at fixed positions and orientations relative to a lens or visor in the AR device, the computer system implements a static transform—corresponding to these known relative positions and orientations of the cameras—to project the virtual surgical environment (or one or more virtual surgical objects within the virtual surgical environment) onto the surgeon's field of view, as shown in FIG. 1. In this implementation, by aligning virtual objects in the virtual surgical environment to real objects represented in images recorded by cameras in the AR device in Block S210, the computer system, thus, aligns the virtual surgical environment to the field of view of these cameras. Furthermore, because these cameras are fixed in the AR device at known positions and orientations relative to a lens or visor in the AR device, the computer system can implement a static transform to capture a 2D or 3D perspective of the virtual surgical environment aligned to the surgeon's field of view. The computer system can thus generate a 2D or 3D AR frame showing the target real cut trajectory from this 2D or 3D perspective of the virtual surgical environment in Block S280.

In another implementation in which the computer system retrieves images recorded by cameras physically disconnected from the AR device, the computer system can calculate a transform for the current virtual surgical environment based on a current position of the AR device (or a lens or visor in the AR device) relative to the cameras before applying this transform to the virtual surgical environment to generate an AR frame. For example, the computer system can implement object recognition techniques to identify the AR device (or the surgeon's eyes, etc.) in a current image of the surgical field, determine the relative position and orientation of the AR device (or the surgeon's eyes, etc.) in the surgical field, and calculate the transform accordingly. In another example: optical fiducials can be arranged within the surgical field; cameras arranged over an operating table can serve images of the optical field to the computer system; the AR device can include an integrated camera that captures and uploads reference images to the computer system; and the computer system can transform the current image of the surgical field into a 3D surgical field image in Block S290, identify the optical fiducials in the current 3D surgical field image, identify these same optical fiducials in a current reference image received from the AR device camera at approximately the same time, match the optical fiducials in the current 3D surgical field image and the current reference image, and calculate the transform that maps the optical fiducials from the 3D surgical field image to the optical fiducials in the reference image. The computer system can then apply the transform to the current virtual surgical environment to generate a 2D or 3D AR frame substantially in real-time. However, the computer system can implement any other method or technique to generate an AR frame representing one or more virtual surgical objects in a perspective of the virtual surgical environment corresponding to the surgeon's current field of view.

The computer system can then serve the AR frame to the surgeon's AR device substantially in real-time. For example, the foregoing Blocks of the second method S200 can be executed by a local computer system, and the local computer system can upload the AR frame to the AR device over wireless communication protocol or over a wired connection. Upon receipt of the AR frame, the AR device can project the AR frame onto a lens or visor in the AR device or onto the surgeon's eye(s) for visual consumption by the surgeon substantially in real-time.

The computer system can therefore cooperate with the AR device to augment the surgeon's field of view of a real surgical field with a virtual representation of a surgical guide snapped to (e.g., located by) a tissue of interest in the surgical field, the surgical guide providing feedback to the surgeon about location of a surgical cutting tool, the real artificial component for implantation, the position of the tissue of interest, and/or any other component within the surgical field. Thus, the computer system can implement Blocks of the second method S200 to, in real-time, plan and accurately execute a surgical operation while limiting dependency of real components to facilitate accuracy of a surgical operation.

The computer system can implement similar methods and techniques to those of the first method S100 to locate a virtual artificial component—such as a virtual artificial femoral component of a complete artificial knee system or of a femoral head component of an artificial hip implant—within the virtual surgical environment and to generate an AR frame showing the virtual artificial component aligned with a tissue of interest in a surgeon's field of view in order to guide the surgeon in placing a real artificial component in a patient. For example, the computer system can generate a virtual outline of the artificial femoral component of an artificial knee system identifying the target real location for the artificial femoral component in the surgical field and publish the virtual outline of the artificial femoral component with the frame to the display overlaid on the image of the patent.

In another example implementation of the second method S200, the computer system can capture the image of the surgical field with a camera attached to a virtual reality headset from a first real viewing location; calculate a view of the surgical field from a particular viewing location in the surgical field to a focal point in the surgical field; define a virtual perspective of the custom virtual anatomical model from a virtual location corresponding to the particular viewing location in the surgical field directed toward a virtual focal point corresponding to the focal point in the surgical field; generate the frame depicting a projection of the target real cut trajectory based on a projection of the virtual cut trajectory from the virtual perspective; and render the frame depicting the projection on a display. In this example, the perspective of the frame rendered in the display can be defined from a location of a camera—offset from the display—toward the surgical field. Alternatively, the perspective of the frame can defined from a location of the display—offset from the camera—to the surgical field. Thus, in order to render a frame in the display perspective, the computer system can transform (or project) the camera perspective of the surgical field onto the display perspective. Additionally, a surgeon may view a different viewing perspective of the surgical field from the surgeon's perspective, the camera's perspective, and the display's perspective. The computer system can transform (or project) the camera perspective of the surgical field onto any other perspective specified by the computer system and/or an operator of the computer system.

2.7 Registration Deviations

As shown in FIG. 5, the computer system an implement another variation of the second method S200 to track intra-operative deviations from surgical plans, including: calculating a target cut trajectory for a surgical cutting tool; capturing a sequence of images of surfaces within an operating room in Block S220; in a first image in the sequence of images captured at a first time, detecting a region of a patient's body designated in the surgical plan in Block S230; detecting a modification to the patient's body based on a difference between the region of the patient's body in the first image and a corresponding region of the patient's body in a second image in the sequence of images captured at a second time succeeding the first time in Block S240; quantifying a difference between the target cut trajectory and the modification in Block S250; and serving guidance based on the difference to a surgeon in real-time in Block S260. The second method S200 can further include confirming the difference based on a post-operative scan of the region of the patient's body.

The computer system can also execute Blocks of the second method S200 to track a region of a patient's body during a surgery; to detect surgical modifications to the region of the patient's body in real-time from depth and/or color images recorded within an operating room during the surgery; to compare a detected surgical modification to a surgical plan defined prior to or during the surgery; and to indicate quantitative differences (or "deviations") between the surgical plan and a current outcome of the surgery to a surgeon substantially in real-time. The computer system can present such quantitative differences to a surgeon substantially in real-time by generating a sequence of AR frames containing a virtual tissue model or a virtual implant model located by a reference on the patient's body in the surgeon's field of view according to the surgical plan; by viewing both the virtual tissue model or the virtual implant model in the same field of view, the surgeon can quickly and visually ascertain a real difference between the surgical plan and the current state of the surgery. The computer system can additionally or alternatively merge a pre-existing surgical plan with real positions of patient tissue, implant components, surgical tools, surgical guides, etc.—identified in a sequence or feed of images recorded during the surgery—into quantitative values for rotational and translational differences between the surgical plan and the current state of the surgery; and the computer system can serve these metrics to the surgeon substantially in real-time, such as through an AR headset or through a monitor arranged within the operating room, in order to inform the surgeon of deviations that may not be visually resolvable by the human eye at the surgeon's working distance from the patient. Furthermore, by generating and storing quantitative data pertaining to a surgical plan for a surgery and deviations from this surgical plan upon completion of a surgery, the computer system can enable data transfer between experienced and inexperienced surgeons, from teachers to medical students, between researchers, etc. substantially without manual feedback from or labeling by surgeons or nurses.

A computer system executing Blocks of the variation of the second method S200 during a surgery can: detect features representative of a particular region of a patient's body designated for the surgery; to register the particular region of the patient's body to the surgical field; to map a virtual tissue model to the particular region of the patient's body; to detect and track real placement of a cutting tool on the patient, a real location of a cut plane on a patient's tissue, and/or placement of an implant device within the patient's body relative to a reference structure within the patient's body in a feed of depth and color images of a surgical field. The computer system can also implement computer vision techniques to calculate differences between a target cut plane and/or a target real location of an implant device defined in the surgical plan and the actual placement of a cut and/or the actual location of the implant device installed in the patient in real-time, and the computer system can provide such feedback to the surgeon in real-time. Furthermore, the computer system can quantify a surgery based on such differences without necessitating additional intra-operative or post-operative feedback or input from a surgeon or nurse.

Once the patient scan data is thus transformed into a patient-specific virtual tissue model, the computer system can automatically retrieve virtual models of one or more implant devices, surgical tools, surgical guides, surgical fasteners, etc. and place these within the patient-specific virtual tissue model (or within the 3D point cloud, or within the 3D scan data, etc.) based on a type of surgery selected by the surgeon. In the foregoing example in which the surgery is a total knee replacement, the computer system can retrieve virtual models for an artificial femoral component, an artificial tibial component, an artificial patellar component, a femoral cutoff guide, and/or a tibial cutoff guide. In this example, the computer system can then automatically place the artificial femoral, tibial, and patellar components in target implant positions within the patient-specific virtual tissue model based on locations of the original human femur, tibia, and patella within the patient-specific virtual tissue model. The computer system can then serve the patient-specific virtual tissue model with the artificial femoral component, the artificial tibial component, and the artificial patellar component positioned accordingly on the virtual femur and virtual tibia in the patient-specific virtual tissue model to the surgeon through the surgeon portal. The computer system can also determine target real locations of the femoral and tibial cutoff guides relative to the femur and tibia in the patient-specific virtual tissue model to achieve these initial artificial femoral, tibial, and patellar component positions; and the computer system can serve the patient-specific virtual tissue model—with the femoral cutoff guide and the tibial cutoff guide in these target real locations relative to the virtual femur and the virtual tibia—to the surgeon through the surgeon portal, as shown in FIG. 5.

Alternatively, the computer system can define target real locations of cut planes relative to the femur and tibia in the patient-specific virtual tissue model to achieve bone removal sufficient to achieve these target artificial femoral, tibial, and patellar component positions, as shown in FIG. 5. The computer system can similarly define cutting tool trajectories relative to the femur and tibia in the patient-specific virtual tissue model that, when executed with a real surgical saw, yield bone removal sufficient to achieve the foregoing target artificial femoral, tibial, and patellar component positions. The computer system can thus serve the patient-specific virtual tissue model—with the virtual cut planes and/or with a virtual cutting tool animated along the cutting tool trajectories in the patient-specific virtual tissue model—to the surgeon through the surgeon portal. The surgeon can then accept or modify these target real locations of the artificial femoral component, the artificial tibial component, the artificial patellar component, the cut planes, and/or the cutting tool trajectories through the surgeon portal. The computer system can thus automatically construct a virtual surgical environment depicting virtual patient tissue and locating one or more virtual surgical objects relative to the virtual patient tissue.

The computer system can additionally or alternatively interface with the surgeon through the surgeon portal to: manually identify discrete tissues in patient scan data; to align a generic virtual anatomical model to patient scan data; to locate one or more virtual implant devices, surgical tools, surgical guides, surgical fasteners, etc. relative to the patient's scan data or relative to an object in a patient-specific virtual tissue model; and/or to define a cut plane or a cutting tool trajectory for an upcoming surgery. The computer system can thus construct a virtual surgical environment depicting both patient tissue and one or more virtual surgical objects based on patient data and/or data entered by a surgeon, radiologist, etc. However, the computer system can implement any other method or technique to automatically—or with guidance from one or more surgeons, radiologists, nurses, etc.—generate a virtual 3D (or 2D, or 4D) model defining a surgical plan for an upcoming surgery in Block S210. The computer system can also implement similar methods and techniques to identify, dimension, and generate surgical plans directed toward soft tissues, such as muscle, tendons, or cartilage.

2.8 Tissue Modification

Block S240 of the second method S200 recites detecting a modification to the patient's body based on a difference between the region of the patient's body in the first image and a corresponding region of the patient's body in a second image in the sequence of images captured at a second time succeeding the first time; and Block S250 of the second method S200 recites quantifying a difference between the surgical plan and the modification. Generally, in Blocks S210 and S220, the computer system identifies an operation performed on a particular tissue during the surgery from a feed of 3D surgical field images, compares this operation to a surgical plan, and calculates differences therebetween.

In one implementation, once the computer system detects a target tissue within the surgical field shown in a 3D surgical field image, as described above, the computer system tracks this target tissue over subsequent 3D surgical field images generated throughout the surgery. Later, the computer system can implement methods and techniques described above to identify and track a cutting tool within the surgical field and to register the cutting tool within the operating room. For example, a surgeon can manipulate a cutting tool including one or more optical fiducials, and the computer system can record the trajectory of the tool relative to the operating room coordinate system. By crossing a vector describing the position of the target tissue relative to the operating room coordinate system with a vector describing the trajectory of the cutting tool relative to the operating room coordinate system at a like time, the computer system can calculate the trajectory of the cutting tool relative to the target tissue. By then projecting a known cutting plane or cutting axis of the tool onto the trajectory of the cutting tool relative to the target tissue, the computer system can calculate a cut plane through the target tissue and thus a geometry of tissue removed from the patient. The computer system can therefore implement methods and techniques described above to track the real trajectory of a cutting tool and to calculate a real position of a cut—relative to a feature of the patient's body—made by the cutting tool in Block S240.

The computer system can additionally or alternatively detect changes to a target tissue directly. For example, the computer system can implement methods and techniques described above to customize a virtual tissue model representing a target tissue prior to a surgery based on MRI, X-ray, CAT, and/or other patient scan data or in real-time during a surgery based on data collected during a motion procedure, extracutaneous tissue features, and/or features detected in 3D surgical field images once a surgeon opens the patient. Throughout the surgery, the computer system can continue to track the target tissue in 3D surgical field images; for small detected differences in the target tissue from one 3D surgical field image to the next, the computer system can average, merge, or weight target tissue data extracted from these 3D surgical field images to update or modify the virtual tissue model. However, for more significant changes to the target tissue detected from one 3D surgical field image to the next (or over a set of 3D surgical field images spanning several seconds or minutes), the computer system can identify such change in the geometry of the target tissue as an operation on the target tissue. The computer system can then generate a second virtual tissue model representing this operation on the target tissue or generate a mask for the current virtual tissue model that represents this operation based on a new geometry of the target tissue extracted (e.g., extrapolated) from subsequent 3D surgical field images, such as by again implementing methods and techniques described above. For example, the computer system can generate and refine a virtual femur model based on pre-operative scan data and femur geometry data extracted from a sequence of 3D surgical field images generated during the surgery prior to an operation on the patient's femur. Once a portion of the medial femoral condyle is removed from the patient's femur, the computer system can calculate a real position of a cut through the femur—relative to the femur, to another feature on the patient's body, or to the operating room coordinate system—directly based on a new surface appearing in subsequent 3D surgical field images.

In one example, the computer system can, in response to a difference between a current cutting position of the surgical tool and the target real cut trajectory of the surgical tool, define a predicted cut trajectory of the surgical tool; define a new cut trajectory amending (i.e., correcting) the predicted cut trajectory to align with the original virtual cut trajectory; define a second target real cut trajectory for the surgical tool in the surgical field based on the new cut trajectory; update the frame to depict the second target real cut trajectory of the surgical tool in the surgical field, the frame identifying the predicted cut trajectory; and publish the frame depicting the second target real cut trajectory of the surgical tool in the surgical field in a display. Thus, the computer system can, in real-time, provide feedback to a surgeon in response to an error and aid in correcting the error.

The computer system can additionally or alternatively identify an implant device within the surgical field and calculate the position of the implant device within the patient—such as relative to the target tissue or to the operating room coordinate system—by processing 3D surgical field images as described above. For example, the computer system can: implement template matching to identify an artificial femoral component of a complete artificial knee system within a 3D surgical field image once a surgeon moves the artificial femoral component into the surgical field; and then extrapolate the position of the artificial femoral component relative to the patient's femur from a 3D surgical field image generated at a later time during the surgery, such as once the surgeon or a nurse provides audible feedback (e.g., an oral command), visual feedback (e.g., a hand gesture), or haptic feedback (e.g., selection of a confirmation button or input region on a connected device) that installation of the artificial femoral component is complete. The computer system can also calculate the position of an implant device relative to a target tissue prior to completion of its installation on the target tissue, such as in order to guide a surgeon in locating the implant device within the patient as described below.

The computer system can therefore detect and track a surgical tool, a target tissue, an implant device, and/or any other feature within the surgical field representative of a modification of or other operation on a target tissue in Block S240.

The computer system can then calculate differences between a target modification or operation on a target tissue—defined in a surgical plan generated pre-operatively in the first method S100 and intraoperatively in the second method S200—and an actual cut plane, section of removed tissue, and/or implant device position determined from 3D surgical field images generated during the surgery. For example, the computer system can project an actual cut plane—relative to the target tissue or the operating room coordinate system, etc. and calculated from a trajectory of a cutting tool within the surgical field—into the virtual surgical environment and then calculate rotational and translation offsets in six degrees of freedom between this actual cut plane and a corresponding target cut plane defined for the target tissue in the virtual surgical environment according to the surgical plan. Similarly, the computer system can generate a second virtual tissue model or a mask for the original virtual tissue model representing an actual section of tissue removed from the target tissue, as described above, insert the second virtual tissue model or the mask into the virtual surgical environment, and then calculate rotational and translation offsets in six degrees of freedom, planarity differences, parallelism differences, surface finish differences, etc. between the second virtual tissue model or the mask and a corresponding virtual tissue model of a target tissue end condition defined in the virtual surgical environment according to the surgical plan. Furthermore, the computer system can locate a virtual implant device model into the virtual surgical environment according to a relative location of the implant device within the operating room, as calculated from a 3D surgical field image, and then calculate rotational and translation offsets in six degrees of freedom between the virtual implant device model and implant device location parameters defined in the surgical plan.

The computer system can thus generate linear distance values, angular distance values, surface finish value, and other dimensioning and tolerancing values quantifying differences between target and actual cut planes, removed tissue geometries, and/or implant device positions, etc. in Block S250. The computer system can generate these quantitative values in real-time during a cutting procedure, during removal of tissue, during location of an implant device, etc. in Block S250, and the computer system can serve these data to the surgeon in real-time during the surgery. The computer system can additionally or alternatively calculate these quantitative values upon completion of an operation. However, the computer system can implement any other method or technique to calculate differences between target and actual operations performed on a patient based on 3D surgical field images generated during a surgery.

2.9 Guidance

Block S260 of the second method S200 recites serving guidance to the surgeon in real-time based on the difference between the surgical plan and the modification. Generally, in Block S260, the computer system can serve differences between target and actual operations performed on a patient—calculated in Block S250—to a surgeon or nurse, etc. during the surgery.

In one implementation, the computer system generates AR frames containing virtual guidance, such as including a virtual representation of a target location of a surgical cutting tool, a target location of a surgical cutting guide, a target cut plane, or a target real location of an implant device located by the corresponding target tissue shown in the surgeon's field of view. In this implementation, based on a current stage of the surgery, the computer system can augment an AR frame with labels for positional differences between the target and actual locations of a cutting tool, then of a cut plane, then of a cut surface of a target tissue, and then of an implant device; by serving such an AR frame to a surgeon's AR headset, the computer system can thus enable the surgeon to both view virtual representations of target real locations of such features and linear distance values, angular distance values, and other dimensioning and tolerancing values quantifying differences between the surgical plan and actual outcome of the surgery simultaneously.

The computer system can therefore serve quantitative values representing differences between the target and actual position or trajectory of a cutting tool within the surgical field or between the target and actual geometry of a cut surface of a tissue to a surgeon in order to guide the surgeon in determining whether a target cut geometry on the tissue has been met (within a preset tolerance) and/or to guide the surgeon in editing the tissue cut. Similarly, the computer system can serve quantitative values representing differences between the target and actual position of an implant device to a surgeon in order to guide the surgeon in determining whether a target implant device location on a tissue has been met (within a preset tolerance) and/or to guide the surgeon in editing the actual implant device location installed previously.

The computer system can additionally or alternatively serve such metrics to the surgeon, nurse, etc. in the operating room via a 2D display or device other than an AR headset within the operating room. However, the computer system can serve such data for real-time consumption by a surgeon or nurse during a surgery in any other format and through any other pathway in Block S260.

2.10 Feedback

The computer system can record final differences between target parameters defined in a surgical plan—generated preoperatively in the first method S100 and generated intraoperatively in the second method S200—and actual corresponding outcomes of the surgery, and the computer system can collect details related to these differences from a surgeon, such as in the form of intra-operative or post-operative textual notes or oral comments. For example, during a surgery, if the computer system detects a difference between a target implant device location and the actual location of the implant device on a patient's bone, the computer system can prompt a surgeon to either: move the implant device to a position that meets the target implant device location within a preset tolerance; or submit a brief oral explanation for this difference. The computer system can interface with a computing device within the operating room to record the surgeon's response to this prompt. For example, the computer system can interface with an AR headset—including a microphone, headphones, a virtual or real triggering mechanism, and/or input region—worn by the surgeon or with microphones arranged within the operating room.

The computer system can link such response from the surgeon to quantitative values calculated in Block S250 and store these data in a surgical result database in order to populate a dataset including surgical plan deviations and human-entered labels for both impracticality of some deviations and support for other deviations over time.

2.11 Deviation Confirmation

In one variation, the second method S200 further includes confirming the difference based on a post-operative scan of the region of the patient's body. Generally, in this variation, the computer system can augment or confirm quantitative deviation values calculated in Block S250 with post-operative X-ray, MRI, CAT, and/or other patient scan data.

In one implementation, the computer system implements methods and techniques described above to identify tissues, detect features, and extract dimensions and tissue geometries from patient scan data including one or more reference markers (e.g., 1"-diameter steel spheres). In particular, the computer system can transform 2D and/or 3D patient scan data into a post-operative virtual patient model representing the patient's limb (or other bodily region) following the surgery, including scaled and dimensioned virtual tissue models and an implant device model adjusted for unique relative tissue and implant device locations extracted from the patient scan data. The computer system can then compare the post-operative virtual patient model to the surgical plan to quantify and confirm deviations from the surgical plan and augment surgical records for the surgery with these data, which may be more precise than quantitative values generated from 3D surgical field images in Block S250. The computer system can therefore process post-operative patient scan data to confirm whether the surgical plan was achieved and to what degree, thereby enabling surgeons and medical staff to identify possible causes for short-term and long-term patient complications stemming from the surgery and/or shortcomings of the surgical plan. Similarly, the computer system can show the post-operative virtual patient model overlaid over pre-operative patient scan data—such as patient scan data generated days, weeks, months or years before the operation—within a surgeon portal to enable the surgeon to compare the patient's pre-operative anatomy to the final position of an implant within the patient.

The computer system can also compare the post-operative virtual patient model to a stored intra-operative virtual surgical model to quantify differences between relatively high-precision post-operative scan data and (possibly) lower-precision intra-operative tissue and implant device location data generated from 3D surgical field images generated through the surgery; the computer system can then implement such relatively high-precision post-operative scan data as labeled data to train a model for calculating relative positions of features and implant devices from a stream of 3D surgical field images during a surgery.

The computer systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer system-readable medium can be stored on any suitable computer readable media such as RAMs, ROMs, flash memory, EEPROMs, optical devices (CD or DVD), hard drives, floppy drives, or any suitable device. The computer system-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for augmenting a surgical field with virtual guidance content comprising:
   combining a scan, representing a tissue of interest of a patient, with a generic virtual anatomical model to define a custom virtual anatomical model of the tissue of interest;
   defining a position of a virtual surgical implant within the custom virtual anatomical model;
   aligning a virtual cut surface, defined by a virtual surgical guide, to the custom virtual anatomical model based on the position of the virtual surgical implant in the custom virtual anatomical model;
   during a surgical operation on the tissue of interest of the patient:
      detecting the tissue of interest in an image of a surgical field captured by a sensor in the surgical field;
      aligning the custom virtual anatomical model to the tissue of interest detected in the image;
      defining a target real location for a real surgical guide in the surgical field based on a virtual location of the virtual surgical guide aligned to the custom virtual anatomical model, the real surgical guide represented by the virtual surgical guide;
      detecting a location of the real surgical guide in the surgical field;
      calculating a guide offset between the location of the real surgical guide and the target real location relative to the tissue of interest;
      in response to the guide offset exceeding a threshold offset, outputting a prompt for an explanation of the guide offset; and
      recording:
         a quantitative value representing the guide offset; and
         the explanation of the guide offset.

2. The method of claim 1, further comprising, during the surgical operation:
   generating an overlay frame representing the target real location of the surgical guide aligned to the tissue of interest in the field of view of the augmented reality headset; and
   rendering the overlay frame on an eyes-up display integrated into an augmented reality headset.

3. The method of claim 2, wherein rendering the overlay frame representing the target real location of the surgical guide in the surgical field comprises:
   aligning the overlay frame to a surgeon's field of view by applying a known transform of the overlay frame of the surgical field from a headset camera of the augmented reality headset to the surgeon's eyes; and
   rendering the transformed overlay frame through the eyes-up display of the augmented reality headset.

4. The method of claim 1, further comprising, during the surgical operation:
   generating an image depicting the target real location of the surgical guide in the surgical field;
   overlaying the image onto and aligned to the image of the surgical field to generate an overlay frame; and
   publishing the frame to a monitor display adjacent the surgical field.

5. The method of claim 1:
   wherein combining the scan, representing a tissue of interest of the patient with a generic virtual anatomical model to define a custom virtual anatomical model comprises:
      combining a scan of a knee region of the patient comprising the tibiofemoral joint, a femur, a tibia, and a patella with a virtual model of an artificial femoral implant, an artificial tibial implant, and an artificial patellar implant;
   wherein aligning the virtual cut surface to the custom virtual anatomical model comprises:
      defining a first cut trajectory in the custom virtual anatomical model for resecting a femoral head of the femur adjacent the tibiofemoral joint and replacing the femoral head with the artificial femoral implant;
      defining a second cut trajectory in the custom virtual anatomical model for resecting a tibial head of the tibia adjacent the tibiofemoral joint and replacing the tibial head with the artificial tibial implant;
   wherein detecting the tissue of interest in the image comprises detecting the femur, the tibia, the patella, and the tibiofemoral joint of the patient in the image;
   wherein defining the target real location for the real surgical guide in the surgical field comprises:
      defining a first target real location for a first real surgical guide in the surgical field based on a virtual location of the first virtual surgical guide aligned to the custom virtual anatomical model, the first real surgical guide represented by the first virtual surgical guide, the first target real location adjacent the femur in the surgical field;

defining a second target real location for a second real surgical guide in the surgical field based on a virtual location of the second virtual surgical guide aligned to the custom virtual anatomical model, the second real surgical guide represented by the second virtual surgical guide, the second target real location adjacent the tibia in the surgical field.

6. The method of claim 1, wherein generating the guide frame indicating the real offset comprises:
generating the guide frame comprising:
visual indicators for a translation and a rotation of the real surgical guide to reduce the guide offset; and
a quantitative value representing the guide offset.

7. The method of claim 1, further comprising, during the surgical operation on the tissue of interest of the patient:
in response to detecting a real surgical cut surface on the tissue of interest in the surgical field:
calculating a cut offset between the real surgical cut surface relative to the tissue of interest and the virtual cut surface relative to the custom virtual anatomical model;
in response to the cut offset exceeding a threshold distance, generating an overlay frame comprising a visual representation of the cut offset and the virtual cut surface relative to the tissue of interest; and
rendering the overlay frame on the display.

8. The method of claim 1:
wherein detecting the tissue of interest in the image comprises detecting the tissue of interest in a first position in the image;
further comprising:
generating a first overlay frame depicting the target real location of the surgical guide in the surgical field and aligned to a viewing perspective based on the first position;
detecting the tissue of interest in a second position in the surgical field, the second position differing from the first position;
aligning the custom virtual anatomical model to the tissue of interest in the second position;
defining a second target real location for the real surgical guide in the surgical field based on a second virtual location of the virtual surgical guide aligned to the custom virtual anatomical model;
generating a second overlay frame depicting the second target real location of the surgical guide in the surgical field and aligned to a viewing perspective; and
rendering the second overlay frame on a display.

9. The method of claim 1:
wherein the virtual model defining the position of the virtual surgical implant within the custom virtual anatomical model comprises defining the position of the virtual surgical implant within the custom virtual anatomical model according to commands entered manually into a surgeon portal; and
wherein aligning a virtual cut surface comprises calculating a cut trajectory automatically based on a geometry of the virtual surgical implant in response to receipt of confirmation of a location of the virtual surgical implant relative to the custom virtual anatomical model at the surgeon portal.

10. The method of claim 1:
wherein detecting a location of the real surgical guide in the surgical field further comprises, detecting an angular orientation of the real surgical guide and a linear position of the real surgical guide in the surgical field;
wherein calculating a guide offset between the location of the real surgical guide and the target real location relative to the tissue of interest further comprises:
calculating an angular offset between the angular orientation of the real surgical guide and the target real location; and
calculating a linear offset between the linear position of the real surgical guide and the target real location.

11. The method of claim 1, further comprising:
recording a label describing the implant offset; and
populating a dataset with:
the quantitative value representing the implant offset;
the explanation of the implant offset; and
the label describing the implant offset.

12. The method of claim 1, further comprising:
defining a virtual cut surface along a boundary of an intersection between the virtual surgical implant and the custom virtual anatomical model of the tissue of interest;
during the surgical operation on the tissue of interest of the patient:
defining a target real cut surface based on the virtual cut surface;
detecting a real cut surface on the tissue of interest;
calculating a cut offset between the real cut surface and the target real cut surface;
in response to the cut offset exceeding a threshold offset, outputting a prompt for an explanation of the cut offset; and
recording:
a quantitative value representing the cut offset; and
the explanation of the cut offset.

13. The method of claim 12, further comprising, during the surgical operation on the tissue of interest of the patient:
defining a target real location for a real surgical implant in the surgical field based on the virtual location of the virtual surgical implant, the real surgical implant represented by the virtual surgical implant;
calculating an implant offset between a location of the real surgical implant and the target real location relative to the tissue of interest;
in response to the implant offset exceeding a threshold offset, outputting a prompt for an explanation of the implant offset; and
recording:
a quantitative value representing the implant offset; and
the explanation of the implant offset.

14. A method for augmenting a surgical field with virtual guidance content comprising:
combining a scan, representing a tissue of interest of a patient, with a generic virtual anatomical model to define a custom virtual anatomical model of the tissue of interest;
defining a virtual surgical implant within the custom virtual anatomical model;
defining a virtual cut surface along a boundary of an intersection between the virtual surgical implant and the custom virtual anatomical model of the tissue of interest; and
during the surgical operation on the tissue of interest of the patient:
detecting the tissue of interest in an image of the surgical field captured by a sensor in the surgical field;
aligning the custom virtual anatomical model to the tissue of interest detected in the image;

defining a target real cut surface based on the virtual cut surface;

detecting a real cut surface on the tissue of interest;

calculating a cut offset between the real cut surface and the target real cut surface;

in response to the cut offset exceeding a threshold offset, outputting a prompt for an explanation of the cut offset; and recording:
- a quantitative value representing the cut offset; and
- the explanation of the cut offset.

15. The method of claim 14:

further comprising detecting a mechanical axis of the tissue of interest in the scan;

wherein combining the scan with a generic virtual anatomical model to define the custom virtual anatomical model of the tissue of interest comprises distorting the generic virtual anatomical model into alignment with the scan to define the custom virtual anatomical model by aligning a mechanical axis of the generic virtual anatomical model to the mechanical axis of the tissue of interest in the scan.

16. The method of claim 15, wherein aligning the custom virtual anatomical model to the tissue of interest detected in the image comprises:

identifying a degree of varus angulation, a degree of valgus angulation, a degree of flexion, and a degree of extension of the tissue of interest in the surgical field to calculate a mechanical axis of the tissue of interest in the surgical field; and aligning a mechanical axis of custom virtual anatomical model to the mechanical axis of the tissue of interest in the surgical field.

17. The method of claim 14, wherein combining the scan with the generic virtual anatomical model to define a custom virtual anatomical model of the tissue of interest comprises:

extracting a first point from the set of orthogonal radiographs corresponding to a first discrete location of the tissue of interest;

defining a first virtual point in the generic virtual anatomical model corresponding to the first point from the set of orthogonal radiographs;

extracting a second point from the set of orthogonal radiographs corresponding to a discrete location of the tissue of interest;

defining a second virtual point in the generic virtual anatomical model corresponding to the second point from the set of orthogonal radiographs;

scaling the generic virtual anatomical model to define the custom virtual anatomical model, wherein a distance between the first virtual point and the second virtual point in the custom virtual anatomical model corresponds to a real distance between the first point and the second point in the set of orthogonal scans.

18. The method of claim 14, wherein detecting the tissue of interest in the surgical field comprises sequentially detecting the surgical field, the patient, a section of the patient comprising vascular and neuromuscular components surrounding the tissue of interest, and the tissue of interest comprising bone over a sequence of images recorded by the sensor during the surgical operation.

19. The method of claim 14:

wherein defining the target real cut surface for the real surgical tool in the surgical field comprises:
- locating a virtual cut axis relative to the tissue of interest and depicted by a line based on a position of the virtual cut trajectory relative to the custom virtual anatomical model; and
- locating a virtual cut stop relative to the tissue of interest and depicted by a point based on the position of the virtual cut surface relative to the custom virtual anatomical model; and further comprising generating an overlay frame comprising the line and the point projected onto a field of view of a surgeon in the surgical field.

20. The method of claim 14, further comprising:

recording a label describing the cut offset; and populating a dataset with:
- the quantitative value representing the cut offset;
- the explanation of the cut offset; and
- the label describing the cut offset.

21. A method for augmenting a surgical field with virtual guidance content comprising:

combining a scan, representing a tissue of interest of a patient, with a generic virtual anatomical model to define a custom virtual anatomical model of the tissue of interest;

defining a position of a virtual surgical implant within the custom virtual anatomical model;

during a surgical operation on the tissue of interest of the patient:
- detecting the tissue of interest in an image of a surgical field captured by a sensor in the surgical field;
- aligning the custom virtual anatomical model to the tissue of interest detected in the image;
- defining a target real location for a real surgical implant in the surgical field based on the virtual location of the virtual surgical implant, the real surgical implant represented by the virtual surgical implant;
- calculating an implant offset between a location of the real surgical implant and the target real location relative to the tissue of interest;
- in response to the implant offset exceeding a threshold offset, outputting a prompt for an explanation of the implant offset; and
- recording:
  - a quantitative value representing the implant offset; and
  - the explanation of the implant offset.

* * * * *